US008273712B2

(12) United States Patent
Kelly

(10) Patent No.: US 8,273,712 B2
(45) Date of Patent: Sep. 25, 2012

(54) PROMOTING WOUND HEALING BY ADMINISTERING A PROSTAGLANDIN E AND GRANULOCYTE-MACROPHAGE COLONY STIMULATING FACTOR

(75) Inventor: Rodney Kelly, Edinburgh (GB)

(73) Assignee: Medical Research Council, Swindon, Wiltshire (GB)

( * ) Notice: Subject to any disclaimer, the term of this patent is extended or adjusted under 35 U.S.C. 154(b) by 238 days.

(21) Appl. No.: 12/094,322

(22) PCT Filed: Nov. 24, 2006

(86) PCT No.: PCT/GB2006/004404
§ 371 (c)(1),
(2), (4) Date: May 20, 2008

(87) PCT Pub. No.: WO2007/060453
PCT Pub. Date: May 31, 2007

(65) Prior Publication Data
US 2008/0317705 A1    Dec. 25, 2008

(30) Foreign Application Priority Data

Nov. 26, 2005  (GB) ................................. 0524103.9

(51) Int. Cl.
*A61K 38/19* (2006.01)
*C07K 14/53* (2006.01)
*C07K 14/535* (2006.01)
(52) U.S. Cl. ........ 514/7.6; 530/350; 530/351; 514/18.6; 514/18.7; 514/21.2
(58) Field of Classification Search .................. None
See application file for complete search history.

(56) References Cited

U.S. PATENT DOCUMENTS

| 4,127,612 | A | 11/1978 | Kluender et al. |
| 4,460,369 | A | 7/1984 | Seymour |
| 5,229,496 | A | 7/1993 | Deeley et al. |
| 5,391,485 | A | 2/1995 | Deeley et al. |
| 5,393,870 | A | 2/1995 | Deeley et al. |
| 5,602,007 | A | 2/1997 | Dunn et al. |
| 5,662,924 | A | 9/1997 | Rhodes |
| 5,792,089 | A | 8/1998 | Penrose et al. |
| 6,191,335 | B1 | 2/2001 | Robinson |
| 6,251,423 | B1 | 6/2001 | Bradford |
| 7,052,684 | B2 * | 5/2006 | Ferguson ..................... 424/85.1 |
| 2004/0034357 | A1 | 2/2004 | Beane et al. |
| 2004/0259863 | A1 * | 12/2004 | Eggenweiler et al. ..... 514/223.8 |
| 2004/0265268 | A1 * | 12/2004 | Jain ............................... 424/85.1 |

FOREIGN PATENT DOCUMENTS

| EP | 1 097 922 A1 | 5/2001 |
| EP | 1 114 816 A1 | 7/2001 |
| WO | WO 97/05894 A1 | 2/1997 |
| WO | WO 01/24842 A2 | 4/2001 |
| WO | WO 02/22157 A2 | 3/2002 |
| WO | 03/010297 A1 | 2/2003 |
| WO | 03/034900 A2 | 5/2003 |
| WO | 03/047530 A2 | 6/2003 |
| WO | WO 03/073981 A2 | 9/2003 |
| WO | WO 2004/007675 A2 | 1/2004 |
| WO | WO 2004/035083 A2 | 4/2004 |
| WO | WO 2005/044298 A1 | 5/2005 |
| WO | WO 2005/073366 A1 | 8/2005 |

OTHER PUBLICATIONS

Albala, "Fibrin Sealants in Clinical Practice," *Cardiovascular Surgery* 11(S1):5-11 (2003).
Appleton, "Wound Repair: The Role of Cytokines and Vasoactive Mediators," *J. Royal Soc Med* 87(8):501-2 (1994).
Arenberg et al., "Inhibition of Interleukin-8 Reduces Tumorigenesis of Human Non-Small Cell Lung Cancer in SCID Mice," *J. Clin. Invest.* 97(12):2792-2802 (1996).
Arnold et al., "Granulocyte Monocyte-Colony Stimulating Factor as an Agent for Wound Healing," *Journal of Wound Care* 4(9):400-2 (1995).
Bianchi et al., "Local Treatment of Chronic Cutaneous Leg Ulcers with Recombinant Human Granulocyte-Macrophage Colony-Stimulating Factor," *European Academy of Dermatology and Venereology* 16:595-8 (2002).
Broughton et al., "The Basic Science of Wound Healing," *Plast. Reconstr. Surg.* 117(Suppl.):12S-34S (2006).
Broughton et al., "Wound Healing: An Overview," *Plast. Recontr. Surg.* 117:1eS-32eS (2006).
Bryan et al., "Cytokine Gene Expression in a Murine Wound Healing Model," *Cytokine* 31:429-38 (2005).
Brzozowski et al., "Agonist of Peroxisome Proliferator-Activated Receptor Gamma (PPAR-γ): A New Compound with Potent Gastroprotective and Ulcer Healing Properties," *Inflammopharmacology* 13(1-3):317-30 (2005).
Buchsel et al., "Granulocyte Macrophage Colony-Stimulating Factor: Current Practice and Novel Approaches," *Clinical Journal of Oncology Nursing* 6(4):198-205 (2002).
Burger et al., "KSHV-GPCR and CXCR2 Transforming Capacity and Angiogenic Responses are Mediated Through a JAK2-STAT3-Dependent Pathway," *Oncogene* 24:2067-75 (2005).
Cantrell et al., "Cloning, Sequence, and Expression of a Human Granulocyte/Macrophage Colony-Stimulating Factor," *Proc. Natl. Acad. Sci. USA* 82:6250-4 (1985).
Cantürk et al., "The Relationship Between Neutrophils and Incisional Wound Healing, " *Skin Pharmacol Appl Skin Physiol* 14:108-16 (2001).

(Continued)

*Primary Examiner* — Marianne P Allen
(74) *Attorney, Agent, or Firm* — LeClairRyan, a Professional Corporation

(57) ABSTRACT

A method of promoting healing of a wound in a patient, the method comprising administering to the patient (i) a prostaglandin E (PGE) or an agonist thereof and/or an agent that increases the local concentration or effect of PGE and (ii) granulocyte-macrophage colony stimulating factor (GMCSF) or a derivative thereof. Use of (i) a PGE or an agonist thereof and/or an agent that increases the local concentration or effect of PGE and (ii) GMCSF or a derivative thereof in the preparation of a medicament for promoting healing of a wound in a patient. A wound dressing, bandage or fibrin glue comprising (i) a PGE or an agonist thereof and/or an agent that increases the local concentration or effect of PGE and (ii) GMCSF or a derivative thereof.

17 Claims, 11 Drawing Sheets

OTHER PUBLICATIONS

CAS Registry No. 059122-46-2 (1985).
CAS Registry No. 099283-10-0 (1992).
CAS Registry No. 123774-72-1 (1991).
Cetinkaya et al., "Granulocyte Macrophage-Colony Stimulating Factor Improves Impaired Anastomotic Wound Healing in Rats Treated with Intraperitoneal Mitomycin-C," *Surg Today* 35:290-4 (2005).
Cho et al., "Thiazolidinediones as a Novel Class of $NAD^+$-Dependent 15-Hydroxyprostaglandin Dehydrogenase Inhibitors," *Archives of Biochemistry and Biophysics* 405:247-51 (2002).
Clark, "Fibrin Glue for Wound Repair: Facts and Fancy," *Thromb Haemost* 90:1003-6 (2003).
Colditz, "Effect of Exogenous Prostaglandin $E_2$ and Actinomycin D on Plasma Leakage Induced by Neutrophil-Activating Peptide-1 /Interleukin-8," *Immunol. Cell Biol.* 68:397-403 (1990).
Costa et al., "Quick Healing of Leg Ulcers After Molgramostim," *The Lancet* 344:481-2 (1994).
Demirer et al., "Effect of Recombinant Human Granulocyte/Macrophage Colony-Stimulating Factor on the Healing of Colonic Anastomosis in Rats," *Journal of Investigative Surgery* 14:221-5 (2001).
Dinc et al., "Effects of Locally Applied Recombinant Human Granulocyte-Macrophage Colony-Stimulating Factor on Ischemic Bowel Anastomoses in Rat," *Eur Surg Res* 36:59-63 (2004).
Dinc et al., "Locally Applied Granulocyte-Macrophage Colony-Stimulating Factor Improves the Impaired Bowel Anastomoses in Rats with Long-Term Corticosterooid Treatment," *World J. Surg.* 26:1208-13 (2002).
Dinc et al., "The Effects of Locally Injected Granulocyte Macrophage-Colony Stimulating Factor on the Healing of Intraoperatively Irradiated Intestinal Anastomoses in Rats," *J. Exp. Clin. Cancer-Res.* 23:77-82 (2004).
Dipietro et al., "MIP-1α as a Critical Macrophage Chemoattractant in Murine Wound Repair," *J. Clin. Invest.* 101(8):1693-8 (1998).
Einhorn et al., "The Expression of Cytokine Activity by Fracture Callus," *Journal of Bone and Mineral Research* 10:1272-81 (1995).
El Saghir et al., "Pressure Ulcer Accelerated Healing with Local Injections of Granulocyte Macrophage-Colony Stimulating Factor," *J Infect* 35(2):179-82 (1997).
Engelhardt et al., "Chemokines IL-8, GROα, MCP-1, IP-10, and Mig Are Sequentially and Differentially Expressed During Phase-Specific Infiltration of Leukocyte Subsets in Human Wound Healing," *American Journal of Pathology* 153(6):1849-60 (1998).
Eroglu et al., "The Effect of GM-CSF (Granulocyte Macrophage Colony Stimulating Factor) on Doxorubicin Induced Tissue Necrosis and Wound Healing," *Indian Journal of Cancer* 37:153-7 (2000).
Foster et al., "Acute Inflammatory Effects of a Monocyte-Derived Neutrophil-Activating Peptide in Rabbit Skin," *Immunology* 67:181-3 (1989).
Gargett et al., "Focal Vascular Endothelial Growth Factor Correlates with Angiogenesis in Human Endometrium. Role of Intravascular Neutrophils," *Human Rreproduction* 16(6):1065-75 (2001).
Genbank Accession No. D28235.1 (2008).
Genbank Accession No. NM_000584.2 (2009).
Genbank Accession No. NM_000758 (2009).
Genbank Accession No. NM_002704 (2005).
Goede et al., "Induction of Inflammatory Angiogenesis by Monocyte Chemoattractant Protein-1," *Int. J. Cancer* 82:765-70 (1999).
Grant et al., "PGE/cAMP and GM-CSF Synergise to Induce a Pro-Tolerance Cytokine Profile in Monocytic Cell Lines," *Biochemical and Biophysical Research Communications* 331:187-93 (2005).
Groves et al., "Recombinant Human GM-CSF in the Treatment of Poorly Healing Wounds," *Adv Skin Wound Care* 13:107-12 (2000).
Grzybowski et al., "Local Application of G-CSF, GM-CSF and EGF in Treatment of Wounds," *Postepy Hig Med Dosw* 53(1):75-86 (1999) (Abstract only).
Grzybowski et al., "New Cytokine Dressings. II. Stimulation of Oxidative Burst in Leucocytes In Vitro and Reduction of Viable Bacteria Within an Infected Wound," *International Journal of Pharmaceutics* 184:179-87 (1999).
Gulcelik et al., "Locally Applied Molgramostim Improves Wound Healing at Colonic Anastomoses in Rats After Ligation of the Common Bile Duct," *Can J. Surg* 48(3):213-8 (2005).
Hamilton, "GM-CSF in Inflammation and Autoimmunity," *TRENDS in Immunology* 23(8):403-8 (2002).
Hong et al., "Recombinant Human Epidermal Growth Factor (EGF) to Enhance Healing for Diabetic Foot Ulcers," *Annals of Plastic Surgery* 56(4):394-8 (2006).
Hui et al., "Rapid Healing of an Indolent Leg Ulcer with Topical rhGM-CSF," *Aust NZ J Med* 26:420-1 (1996).
Illum et al., "Ulcerated Haemanioma Successfully Treated with Interferon Alfa-2b and Topical Granulocyte-Macrophage Colony-Stimulating Factor," *Dermatology* 191:315-7 (1995).
Jaschke et al., "Recombinant Human Granulocyte-Macrophage Colony-Stimulating Factor Applied Locally in Low Doses Enhances Healing and Prevents Recurrence of Chronic Venous Ulcers," *International Journal of Dermatology* 38:380-6 (1999).
Jing et al., "A Novel Signaling Pathway Mediates the Inhibition o fCCL3/4 Expression by Prostaglandin $E_2$*," *The Journal of Biological Chemistry* 279(53):55176-86 (2004).
Jones, "Future Uses of Granulocyte-Macrophage Colony-Stimulating Factor (GM-CSF)," *Stem Cells* 12(Suppl 1):229-40 (1994).
Jones, "The Effects of rhGM-CSF on Macrophage Function," *Eur J Cancer* 29A(Supp3):S10-S13 (1993).
Jorgensen et al., "Dose-Dependent Impairment of Collagen Deposition by Topical Granulocyte-Macrophage Colony-Stimulating Factor in Human Experimental Wounds," *Annals of Surgery* 236(5):684-92 (2002).
Joyce et al., "$PGE_2$: A Mediator of Corneal Endothelial Wound Repair In Vitro," *The American Physiological Society* pp. C269-C275 (1994).
Jyung et al., "Granulocyte-Macrophage Colony-Stimulating Factor and Granulocyte Colony-Stimulating Factor: Differential Action on Incisional Wound Healing," *Surgery* pp. 325-334 (1994).
Kalka et al., "Angiogenese und Vaskulogenese," *Herz* 25(6):611-22 (2000).
Kalka et al., "Vascular Endothelial Growth Factor (VEGF): Therapeutic Angiogenesis and Vasculogenesis in the Treatment of Cardiovascular Disease," *Med Klin* 94:193-201 (1999).
Kaplan et al., "Novel Responses of Human Skin to Intradermal Recombinant Granulocyte/Macrophage-Colony-Stimulating Factor: Langerhans Cell Recruitment, Keratinocyte Growth, and Enhanced Wound Healing," *J. Exp. Med.* 175:1717-28 (1992).
Karamanoukian et al., "Action of Granulocyte-Macrophage Colony-Stimulating Factor on Incisional Wound Healing in Congenital Neutropenia," *Surgery* pp. 599-600 (1995).
Kim et al., "Inhibition of the Angiogenesis by the MCP-1 (Monocyte Chemoattractant Protein-1) Binding Peptide," *FEBS Letters* 579:1597-1601 (2005).
Koch et al., "Interleukin-8 as a Macrophage-Derived Mediator of Angiogenesis," *Science* 258:1798-801 (1992).
Konturek et al., "Epidermal Growth Factor and Prostaglandin $E_2$ Accelerate Mucosal Recovery from Stress-Induced Gastric Lesions Via Inhibition of Apoptosis," *Journal of Physiology* 95:361-7 (2001).
Lapeyre et al., "Treatment Modalities of Oral Mucosistis After Radiation of Head and Neck Cancers," *Cancer* 5(Suppl 1):121S-130S (2001).
Laudanski et al., "Differential EP4 Surface Expression Regulation May contribute to Altered MO to iDC Differentiation in Trauma Patients Versus Controls," AAI200: Meeting Abstracts p. C201(114.16) (2003).
Lee et al., "Isolation of cDNA for a Human Granulocyte-Macrophage Colony-Stimulating Factor by Functional Expression in Mammalian Cells," *proc. Natl. Acad. Sci. USA* 82:4360-4 (1985).
Leucomax, "Data Sheet," *Information for Professionals* (2002).
Leukine, "Sargramostim," *LEUKINE Package Insert Approved Text* pp. 1-30 (1998).
Li et al., "Up-Regulation of Prostaglandin EP4 Receptor Messenger RNA in Fetal Rabbit Skin Wound," *Arch Otolaryngol Head Neck Surg* 126:1337-43 (2000).
Lionelli et al., "Wound Dressings," *Surg Clin N Am* 83:617-38 (2003).

Low et al., "Wound Healing in MIP1α-/- and MCP-1-/- Mice," *American Journal of Pathology* 159(2):457-63 (2001).
Lundberg et al., "Comparison of IL-10 Levels in Chronic Venous Insufficiency Ulcers and Autologous Donor Tissue," *Arch Dermatol Res* 290:669-73 (1998).
MacGillivray, "Fibrin Sealants and Glues," *J Card Surg* 18:480-5 (2003).
Maekawa et al., "Effect of Granulocyte-Macrophage Colony-Stimulating Factor Inducer on Left Ventricular Remodeling After Acute Myocardial Infarction," *Journal of the American College of Cardiology* 44(7):1510-20 (2004).
Malik et al., "Effect of Subcutaneous Injection of Granulocyte-Macrophage Colony Stimulating Factor (GM-CSF) on Healing of Chronic Refractory Wounds," *Eur J Surg* 164:737-44 (1998).
Mann et al., "Repression of Prostaglandin Dehydrogenase by Epidermal Growth Factor and Snail Increases Prostaglandin $E_2$ and Promotes Cancer Progression," *Cancer Res* 66(13):6649-56 (2006).
Mastroianni et al., "Local Treatment of a Chronic Leg Ulcer with GM-CSF in a Patient with HIV Infection," *Sexually Transmitted Infections*, Letters to the editor, CD-Rom review, Notices, Current publications, Division of Infectious Diseases,, G B Morgani General Hospital, Piazza Solieri, Italy 75(3):203-4 (1999).
Memisoglu et al., "In Vivo for rhGM-CSF Wound-Healing Efficacy in Topical Vehicles," *Pharmaceutical Development and Technology* 2(2):171-80 (1997).
Menaker, :Wound Dressings for Office-Based Surgery, *Facial Plastic Surgery* 20(1):91-105 (2004).
Méry et al., "Topical Effectiveness of Molgramostim (GM-CSF) in Sickle Cell Leg Ulcers," *Dermatology* 208:135-7 (2004).
Milio et al., "Efficacy of the Treatment with Prostaglandin E-1 in Venous Ulcers of the Lower Limbs," *Journal of Vascular Surgeruy* 42(2):304-8 (2005).
Miyatake et al., "Structure of the Chromosomal Gene for Granulocyte-Macrophage Colony Stimulating Factor: Comparison of the Mouse and Human Genes," *The EMO Journal* 4(10)2561-8 (1985).
Mizukami et al., "Induction of Interleukin-8 Preserves the Angiogenic Response in HIF-1α—Deficient Colon Cancer Cells," *Nature Medicine* 11(9):992-7 (2005).
Mueller et al., "Neutrophils Infiltrating the Endometrium Express Vascular Endothelial Growth Factor: Potential Role in Endometrial Angiogenesis," *Fertility and Sterility* 74(1):107-12 (2000).
Muscara et al., "Wound Collagen Deposition in Rats: Effects of an NO-NSAID and a Selective COX-2 Inhibitor," *British Journal of Pharmacology* 129:681-6 (2000).
Ogle et al., "The IL-3 and GM-CSF Mediated Regulation of $PGE_2$ Production by Different Populations of Macrophages," Meeting Abstract from meeting sponsored by the American Association of Immunologists and the International Union of Immunological Societies, San Francisco, CA USA p. 1658 (Jul. 23-29, 1995).
Ogle et al., "Thermal Injury Induces the Development of Inflammatory Macrophages from Nonadherent Bone Marrow Cells," *Inflammation* 21(6):569-82 (1997).
Ohno et al., "Studies on 15-Hydroxyprostaglandin Dehydrogenase with Various Prostaglandin Analogues," *J. Biochem.* 84(6):1485-94 (1978).
Ottonello et al., "Cyclic AMP-Elevating Agents Down-Regulate the Oxidative Burst Induced by Granulocyte-Macrophage Colony-Stimulating Factor (GM-CSF) in Adherent Neutrophils," *Clin Exp Immunol* 101:502-6 (1995).
Park et al., "Growth Related Secretion and Production of GM-CSF by Epithelial Cell Line," *Journal of Dermatological Science* 25:53-8 (2001).
Payne et al., "Long-Term Outcome Study of Growth Factor-Treated Pressure Ulcers," *The American Journal of Surgery* 181:81-6 (2001).
Pierce et al., "Pharmacologic Enhancement of Wound Healing," *Annu. Rev. Med.* 46:467-81 (1995).
Pojda et al., "Treatment of Non-Healing Ulcers with rhGM-CSF and Skin Grafts," *The Lancet* vol. 343 p. 1100 (1994).
Poonam et al., "Cyclo-Oxygenase-2 Expression and Prostaglandin $E_2$ Production in Experimental Chronic Gastric Ulcer Healing," *European Journal of Pharmacology* 519:277-84 (2005).

Proudfoot et al., "Structure and Bioactivity of Recombinant Human CTAP-III and NAP-2," *Journal of Protein Chemistry* 16(1):37-49 (1997).
Raderer et al., "Topical Granulocyte-Macrophage Colony-Stimulating Factor in Patients With Cancer and Impaired Wound Healing," *Journal of the National Cancer Institute* 89(3):260-3 (1997).
Regan, "EP2 and EP4 Prostanoid Receptor Signaling," *Life Sciences* 74:143-53 (2003).
Remington, "The Science and Practice of Pharmacy," 21st Edition, pp. 1392-1395,1406-1416, and 1460 (2005).
Ricketts et al., "Cytokine mRNA Changes During the Treatment of Hypertrophic Scars with Silicone and Nonsilicone Gel Dressings," *Dermatol Surg* 22:955-9 (1996).
Ritz et al., "On the Generation of Allergic Airway Diseases: From GM-CSF to Kyoto," *TRENDS in Immunology* 23(8):396-402 (2002).
Robertson et al., "Granulocyte Macrophage Colony Stimulating Factor (GM-CSF) in the Murine Reproductive Tract: Stimulation by Seminal Factors," *Reprodu. Fertil. Dev.* 2:359-68 (1990).
Robillard et al., "Association of Pregnancy-Induced Hypertension with Duration of Sexual Cohabitation Before Conception," *Lancet* 344:973-5 (1994).
Robillard et al., "Revisiting the Epidemiological Standard of Preeclampsia: Primigravidity or Primipaternity?" *European Journal of Obstetrics and Gynecology* 84:37-41 (1999).
Robson et al., "Sequential Cytokine Therapy for Pressure Ulcers: Clinical and Mechanistic Response," *Annals of Surgery* 231(4):600-11 (2000).
Rubbia-Brandt et al., "Locally applied GM-CSF Induces the Accumulation of a-Smooth Muscle Actin Containing Myofibroblasts," *Virehows Archiv B Cell Pathol* 60-:73-82 (1991).
Rudack et al., "Cytokines in Nasal Polyposis, Acute and Chronic Sinusitis," *American Journal of Rhinology* 12(6):383-8 (1998).
Schaffner et al., "Induction and Antimicrobial Activity of Platelet Basic Protein Derivatives in Human Monocytes," *Journal of Leukocyte Biology* 76:1010-8 (2004).
Schlez et al., "Transdermal Application of Prostaglandin $E_1$ Ethyl Ester for the Treatment of Trophic Acral Skin Lesions in a Patient with Systemic Scleroderma," *European Academy of Dermatology and Venereology JEADV* 16:526-8 (2002).
Senet et al., "Evaluation of the Stability and Efficacy of rhGM-CSF as a Topical Agent in a Gel Formulation," *Journal of Wound Care* 11(4):132-4 (2002).
Senior et al., "Chemotactic Activity of Platelet Alpha Granule Proteins for Fibroblasts," *The Journal of Cell Biology* 96:382-5 (1983).
Shamseddine et al., "Granulocyte Macrophage-Colony Stimulating Factor for Treatment of Chemotherapy Extravasation," *Eur. J. Gynaec. Oncol.* pp. 479-481 (1998).
Sheibanie et al., "Prostaglandin E2 Induces Production in Bone Marrow-Derived Dentritic Cells," *The FASEB Journal* 18:1318-20 (2004).
Siddiqui et al., "Recombinant Granulocyte macrophage Colony Stimulating Factor (rhu-GM-CSF) in the Treatment of Extensive Leg Ulcers: A Case Report," *Surgery* 127:589-92 (2000).
Smith et al., "Initiating the Inflammatory Phase of Incisional Healing prior to Tissue Injury," *Journal of Surgical Research* 92:11-17 (2000).
Spotnitz et al., "Fibrin Sealant Tissue Adhesive-Review and Update," *Journal of Long-Term Effects of Medical Implants* 15(3):245-70 (2005).
Sternfeld et al., "Thermal Injury Functionally Alters Bone Marrow-Derived Macrophages: A Study of Monocyte-Hepatocyte Interactions," *Journal of Burn Care & Rehabilitation* 18(6):505-14 (1997).
Stieter et al., "A Corneal Factor that Induces Neovascularization," *American journal of Pathology* 141(6):1279-84 (1992).
Strieter et al., "The Role of CXC Chemokines as Regulators of Angiogenesis," *Shock* 4(3):155-60 (1995).
Sunderkötter et al., "Macrophages and Angiogenesis," *Journal of Leukocyte Biology* 55:410-22 (1994).
Tanaka et al., "Acceleration of Wound Healing by Gelatin Film Dressings with Epidermal Growth Factor," *J. Vet. Med. Sci.* 67(9):909-13 (2005).

Tang et al., "Surgical Glove Powders Differentially Modulate Macrophage and Lymphocyte-Derived Cytokines and Eicosanoids Production In Vitro," *Wound Repair and Regeneration* 3(4):518-26 (1995).

Tarr, "Granulocyte-Macrophage Colony-Stimulating Factor and the Immune System," *Medical Oncology* 13:133-40 (1996).

Thélu et al., "Notch Signalling is Linked to Epidermal Cell Differentiation Level in Basal Cell Carcinoma, Psoriasis and Wound Healing," *BMC Dermatology* 2(7):1-12 (2002).

Ure et al., "Granulocyte/Macrophage Colony-Stimulating Factor Increases Wound-Fluid Interleukin 8 in Normal Subjects But Does Not Accelerate Wound Healing," *British Journal of Dermatology* 138:277-82 (1998).

Vermeulen et al., "Systematic Review of Dressings and Topical Agents for Surgical Wounds Healing by Secondary Intention," *British Journal of Surgery* 92:665-72 (2005).

Wandi, "GM-CSF in the Treatment of Skin Ulceration in Breast Cancer," *Journal of Wound Care* 6(4):165-6 (1997).

Weissflog et al., "Leukocyte Infiltration and Secretion of Cytokines in Pleural Drainage Fluid After Thoracic Surgery," *Chest* 115:1604-10 (1999).

Wheeler et al., "GM-CSF and Wound Healing," *MJA (Medical Journal of Australia)* 168:580 (1998).

Wiernas et al., "Effects fo Bradykinin on Signal Transduction, Cell Proliferation, and Cytokine, Prostaglandin $E_2$ and Collagenase-1 Release from Human Corneal Epithelial Cells," *British Journal of Pharmacology* 123:1127-37 (1998).

Wollin et al., "Granulocyte-Macrophage Colony-Stimulating Factor Amplifies Lipopolysaccharide-Induced Bronchoconstriction by a Neutrophil- and Cyclooxygenase 2-Dependent Mechanism," *Am J Respir Crit Care Med* 163:443-50 (2001).

Wong et al., "Human GM-CSF: Molecular Cloning of the Complementary DNA and Purification of the Natural and Recombinant Proteins," *Science* 228(4701):810-5 (1985).

Wu et al., "The Effects of Surgery, With or Without rhGM-CSF, on the Angiogenic Profile of Patients Treated for Colorectal Carcinoma," *Cytokine* 25:68-72 (2004).

Quesniaux et al., "Granulocyte-macrophage colony-stimulating factor," In: The Cytokine Handbook, (ed. Angus T. W.) Academic Press pp. 656-58 (1998).

Shimazu, S., "Evaluation of immunosuppressive properties of fluid from healing wounds and influence of prostaglandins," Nippon Geka Gakkai Zasshi 88(12):1667-75 (1987) (English abstract).

Harvey, "Wound Healing, " Orthopaedic Nursing 24(2):143-157 (2005).

Asseman et al., "An Essential Role for Interleukin 10 in the Function of Regulatory T Cells That Inhibit Intestinal Inflammation," J. Exp. Med. 190(7):995-1003 (1999).

* cited by examiner

FIGURE 1A

Human GMCSF cDNA. Genbank Accession No. NM_000758

```
  1 gctggaggat gtggctgcag agcctgctgc tcttgggcac tgtggcctgc agcatctctg
 61 cacccgcccg ctcgcccagc cccagcacgc agccctggga gcatgtgaat gccatccagg
121 aggcccggcg tctcctgaac ctgagtagag acactgctgc tgagatgaat gaaacagtag
181 aagtcatctc agaaatgttt gacctccagg agccgacctg cctacagacc cgcctggagc
241 tgtacaagca gggcctgcgg ggcagcctca ccaagctcaa gggcccttg accatgatgg
301 ccagccacta caagcagcac tgccctccaa ccccggaaac ttcctgtgca acccagacta
361 tcacctttga aagtttcaaa gagaacctga aggactttct gcttgtcatc cctttgact
421 gctgggagcc agtccaggag tgagaccggc cagatgaggc tggccaagcc ggggagctgc
481 tctctcatga acaagagct agaaactcag gatggtcatc ttggagggac caaggggtgg
541 gccacagcca tggtgggagt ggcctggacc tgccctgggc cacactgacc ctgatacagg
601 catggcagaa gaatgggaat attttatact gacagaaatc agtaatattt atatatttat
661 atttttaaaa tatttattta tttatttatt taagttcata ttccatattt attcaagatg
721 ttttaccgta ataattatta ttaaaaatat gcttct
```

FIGURE 1B

Human GMCSF polypeptide. Genbank Accession No. NM_000758

```
  1 MWLQSLLLLG TVACSISAPA RSPSPSTQPW EHVNAIQEAR RLLNLSRDTA AEMNETVEVI
 61 SEMFDLQEPT CLQTRLELYK QGLRGSLTKL KGPLTMMASH YKQHCPPTPE TSCATQTITF
121 ESFKENLKDF LLVIPFDCWE PVQE
``` protein release from monocytic U937 after 48 hr culture mRNA - effect of pretreatment with PGE/GMCSF Wound area measurements on days 3, 7 and 10 post surgery Wound area measurements on day 3 post surgery

Figure 11

Colour of wound observations

| | | | | | | | | | | |
|---|---|---|---|---|---|---|---|---|---|---|
| R | R | R | R | R | B | R | R | R | R | Treatment 1 |
| R | R | R | R | R | R | R | B | R | R | |
| R | R | R | R | R | B | B | B | R | R | |
| R | R | R | R | R | B | ■ | ■ | R | R | |
| R | R | B | B | B | B | B | B | B | B | |
| R | R | Y | Y | B | R | B | B | R | R | |
| ▨ | ▨ | ▨ | ▨ | ▨ | ▨ | ▨ | ▨ | ▨ | ▨ | |
| R | R | B | B | B | R | B | B | R | R | Treatment 2 |
| R | R | B | B | B | B | B | B | B | B | |
| R | R | B | B | B | B | R | R | R | R | |
| R | R | B | B | B | B | ■ | ■ | R | R | |
| R | R | B | B | B | B | B | B | R | R | |
| R | R | B | B | B | R | B | B | B | R | Treatment 3 |
| R | R | B | B | B | B | B | B | B | B | |
| R | R | B | B | B | B | R | R | R | R | |
| R | R | B | B | B | R | B | B | R | R | |
| R | R | B | B | B | R | B | B | R | R | |
| R | R | B | B | B | B | R | R | R | R | |
| R | R | B | B | B | B | B | B | B | B | Treatment 4 |
| R | R | B | B | B | R | B | B | B | B | |
| R | R | B | B | B | B | B | B | B | B | |
| R | R | B | B | B | B | R | R | R | R | |
| R | R | B | B | B | B | R | R | R | B | |
| R | R | B | B | B | B | B | R | B | B | |
| Day 1 | Day 2 | Day 3 | Day 4 | Day 5 | Day 6 | Day 7 | Day 8 | Day 9 | Day 10 | |

| KEY | |
|---|---|
| R | Red |
| B | Brown |
| ▨ | No data |
| ■ | Black |
| Y | Scab yellow |

SEQUENCE LISTING

<160> NUMBER OF SEQ ID NOS: 14

<210> SEQ ID NO 1
<211> LENGTH: 756
<212> TYPE: DNA
<213> ORGANISM: Homo sapiens

<400> SEQUENCE: 1

```
gctggaggat gtggctgcag agcctgctgc tcttgggcac tgtggcctgc agcatctctg      60
cacccgcccg ctcgcccagc cccagcacgc agccctggga gcatgtgaat gccatccagg     120
aggcccggcg tctcctgaac ctgagtagag acactgctgc tgagatgaat gaaacagtag     180
aagtcatctc agaaatgttt gacctccagg agccgacctg cctacagacc cgcctggagc     240
tgtacaagca gggcctgcgg ggcagcctca ccaagctcaa gggccccttg accatgatgg     300
ccagccacta caagcagcac tgccctccaa ccccggaaac ttcctgtgca acccagacta     360
tcacctttga aagtttcaaa gagaacctga aggactttct gcttgtcatc ccctttgact     420
gctgggagcc agtccaggag tgagaccggc cagatgaggc tggccaagcc ggggagctgc     480
tctctcatga acaagagct agaaactcag gatggtcatc ttggagggac caaggggtgg     540
gccacagcca tggtgggagt ggcctggacc tgccctgggc cacactgacc ctgatacagg     600
catggcagaa gaatgggaat attttatact gacagaaatc agtaatattt atatatttat     660
attttaaaa tatttattta tttatttatt taagttcata ttccatattt attcaagatg     720
ttttaccgta ataattatta ttaaaaatat gcttct                                756
```

<210> SEQ ID NO 2
<211> LENGTH: 144
<212> TYPE: PRT
<213> ORGANISM: Homo sapiens

<400> SEQUENCE: 2

```
Met Trp Leu Gln Ser Leu Leu Leu Gly Thr Val Ala Cys Ser Ile
1               5                   10                  15
Ser Ala Pro Ala Arg Ser Pro Ser Pro Ser Thr Gln Pro Trp Glu His
                20                  25                  30
Val Asn Ala Ile Gln Glu Ala Arg Arg Leu Leu Asn Leu Ser Arg Asp
            35                  40                  45
Thr Ala Ala Glu Met Asn Glu Thr Val Glu Val Ile Ser Glu Met Phe
        50                  55                  60
Asp Leu Gln Glu Pro Thr Cys Leu Gln Thr Arg Leu Glu Leu Tyr Lys
    65                  70                  75                  80
Gln Gly Leu Arg Gly Ser Leu Thr Lys Leu Lys Gly Pro Leu Thr Met
                85                  90                  95
```

```
Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
    130                 135                 140

<210> SEQ ID NO 3
<211> LENGTH: 23
<212> TYPE: DNA
<213> ORGANISM: Artificial
<220> FEATURE:
<223> OTHER INFORMATION: Forward PCR primer for Pro-PBP

<400> SEQUENCE: 3
ccaaaaacat ccaaagtttg gaa                                          23

<210> SEQ ID NO 4
<211> LENGTH: 24
<212> TYPE: DNA
<213> ORGANISM: Artificial
<220> FEATURE:
<223> OTHER INFORMATION: Reverse PCR primer for Pro-PBP

<400> SEQUENCE: 4
cagtgtggct atcacttcga cttg                                         24

<210> SEQ ID NO 5
<211> LENGTH: 24
<212> TYPE: DNA
<213> ORGANISM: Artificial
<220> FEATURE:
<223> OTHER INFORMATION: Pro-PBP probe

<400> SEQUENCE: 5
tgatcgggaa aggaacccat tgca                                         24

<210> SEQ ID NO 6
<211> LENGTH: 25
<212> TYPE: DNA
<213> ORGANISM: Artificial
<220> FEATURE:
<223> OTHER INFORMATION: Forward PCR primer for COX-2

<400> SEQUENCE: 6
gtgttgacat ccagatcaca tttga                                        25

<210> SEQ ID NO 7
<211> LENGTH: 23
<212> TYPE: DNA
<213> ORGANISM: Artificial
<220> FEATURE:
<223> OTHER INFORMATION: Reverse PCR primer for COX-2

<400> SEQUENCE: 7
gagaaggctt cccagctttt gta                                          23

<210> SEQ ID NO 8
<211> LENGTH: 33
<212> TYPE: DNA
<213> ORGANISM: Artificial
<220> FEATURE:
<223> OTHER INFORMATION: COX-2 probe

<400> SEQUENCE: 8
tgacagtcca ccaacttaca atgctgacta tgg                               33
```

-continued

```
<210> SEQ ID NO 9
<211> LENGTH: 18
<212> TYPE: DNA
<213> ORGANISM: Artificial
<220> FEATURE:
<223> OTHER INFORMATION: Forward PCR primer for CXCL8

<400> SEQUENCE: 9
ctggccgtgg ctctcttg                                                       18

<210> SEQ ID NO 10
<211> LENGTH: 22
<212> TYPE: DNA
<213> ORGANISM: Artificial
<220> FEATURE:
<223> OTHER INFORMATION: Reverse PCR primer for CXCL8

<400> SEQUENCE: 10
ttagcactcc ttggcaaaac tg                                                  22

<210> SEQ ID NO 11
<211> LENGTH: 29
<212> TYPE: DNA
<213> ORGANISM: Artificial
<220> FEATURE:
<223> OTHER INFORMATION: CXCL8 probe

<400> SEQUENCE: 11
ccttcctgat ttctgcagct ctgtgtgaa                                           29

<210> SEQ ID NO 12
<211> LENGTH: 19
<212> TYPE: DNA
<213> ORGANISM: Artificial
<220> FEATURE:
<223> OTHER INFORMATION: Forward PCR primer for IL-10

<400> SEQUENCE: 12
ctacggcgct gtcatcgat                                                      19

<210> SEQ ID NO 13
<211> LENGTH: 25
<212> TYPE: DNA
<213> ORGANISM: Artificial
<220> FEATURE:
<223> OTHER INFORMATION: Reverse PCR primer for IL-10

<400> SEQUENCE: 13
tggagcttat taaaggcatt cttca                                               25

<210> SEQ ID NO 14
<211> LENGTH: 27
<212> TYPE: DNA
<213> ORGANISM: Artificial
<220> FEATURE:
<223> OTHER INFORMATION: IL-10 probe

<400> SEQUENCE: 14
cttccctgtg aaaacaagag caaggcc                                             27
```

PROMOTING WOUND HEALING BY ADMINISTERING A PROSTAGLANDIN E AND GRANULOCYTE-MACROPHAGE COLONY STIMULATING FACTOR

This application is a national stage application under 35 U.S.C. 371 of PCT/GB2006/004404, filed Nov. 24, 2006, which claims priority to GB 0524103.9, filed Nov. 26, 2005.

The present invention relates to therapeutic compositions methods and uses; in particular it relates to methods and compositions for wound healing.

The process of wound healing is generally considered to consist of three phases: the inflammatory/exudate phase, the proliferative phase, and the differentiation phase. The first of these phases, lasting until approximately the fourth day, is critical and comprises prevention of haemorrhage, release of cytokines and permeability enhancers (leading to local oedema) and cellular ingress. The main cell type to arrive first is the neutrophil which secretes VEGF and is angiogenic (Gargett et al, 2001; Mueller et al, 2000). The main neutrophil attracting agent CXCL8 (IL-8) is also implicated in angiogenesis, although not necessarily directly (Strieter et al, 1992; Strieter et al, 1995). Angiogenesis is critical to wound repair and although neovascularisation is associated with a later stage of the repair process, the delayed effects of CXCL8 are considered essential (Engelhardt et al, 1998).

Neutrophil infiltration is accompanied by a more prolonged increase in macrophage numbers. The expression of CCL2 (MCP-1) is elevated in the first 24 hours after experimental wounding and this is associated with the influx of blood monocytes which are differentiated to macrophages once they have arrived at the site of damage (Engelhardt et al, 1998). This has been confirmed in the CCL2 knockout mouse in which wound repair is deficient (Low et al, 2001).

The chemokine CCL-3 (MIP-1α) is also likely to have an important role in wound repair as seen in a mouse model (DiPietro, 1998) although the knockout mouse does not have any obvious deficiency in repair (Low et al, 2001).

The chemokine CXCL7 (NAP-2), connective tissue activating peptide III (CTAPIII), and beta-thromboglobulin (BTG) are each derived from a common precursor, platelet basic protein (PBP), by post-translational proteolysis. CXCL7 and CTAPIII are both involved in the early stages of wound healing (Proudfoot et al, 1997) and BTG is highly chemotactic for fibroblasts, again important in wound healing (Senior et al, 1983).

Chemokines are usually regarded as pro-inflammatory. However, in an immune response to an insult, chemokines induce the relevant phagocytic and cytokine-secreting cells and play a vital role in both debridement and wound repair. prostaglandin E (PGE) is likely to play multiple roles in its interactions with chemokines since PGE synergises with IL-8 (CXCL8) in attracting neutrophils into tissue (Colditz, 1990; Foster et al, 1989). In chemokine synthesis, PGE is reported as inhibiting the lipopolysaccharide induced synthesis of CCL3 and CCL4 (Jing et al, 2004) and as such PGE might be expected to have inhibitory actions in chemokine synthesis.

Granulocyte-macrophage colony stimulating factor (GMCSF) has an important role in granulocyte and macrophage lineage maturation. GMCSF has been proposed as both a treatment agent and a target for treatment. Recombinant human GMCSF has been used to treat some cancers and to promote haematopoietic reconstitution following bone marrow transplantation (Leukine® Package Insert Approved Text, February 1998, and Buchsel, et al, 2002). By contrast, other recent reports describe GMCSF as being a potential target for treatment of inflammatory and immune diseases (Hamilton, 2002) and asthma Ritz et al, 2002).

The inventor has previously demonstrated a compelling synergism between GMCSF and prostaglandins that raise cAMP levels in monocytes, such as PGE, in the stimulation of IL-10 synthesis and inhibition of IL-12 (Grant et al, 2005; WO 2004/035083). This synergism was due to the ability of PGE to raise cAMP levels via the EP2 and/or the EP4 receptors. The environment of high IL-10 and low IL-12, provided by suitably programmed monocyte/macrophages in response to the action of PGE and GMCSF, induces immunological tolerance. In addition, the inventor has previously demonstrated that this combination of PGE and GMCSF, which induces immunological tolerance, together with stem cells can be used for a variety of therapeutic purposes (Grant et al, 2005; WO 2005/044298).

Sheibanie et al (2004) reported a synergism between PGE and GMCSF in dendritic cells and suggested a combined therapy for autoimmune diseases such as rheumatoid arthritis. This paper deals with the effects of the combination on IL-23 which, although a relatively newly-discovered cytokine, appears to be more like IL-12 than anything else.

Because of the huge concentrations of E series prostaglandins in human seminal plasma, it has been recognised that these agents are likely to be important contributors to immune programming of cells of the female reproductive tract after semen deposition. Clearly spermatozoa are critical to the survival of the species and thus evolutionary pressure would have ensured that no fatal immune response was directed against these allogeneic invaders. Indeed the immune recognition and acceptance of spermatozoa may also facilitate adequate colonisation of the maternal blood vessels by the invading trophoblast (Robillard et al, 1994). The immunological acceptance of spermatozoa may have been particularly difficult when, at some point in evolution, repeated or chronic infections appeared in either male or female the genital tract. A more subtle action of prostaglandins (from semen and elsewhere) may involve interaction with GMCSF, produced by epithelial cells and cells of the lamina propria. In the case of semen deposition, GMCSF synthesis may well be stimulated by the actions of TGFβ (Robertson & Seamark, 1990) which is found in high levels in human seminal plasma.

In a continuation of these immunological fertility studies, the inventor studied the effects of a combination of human seminal plasma (HSP) and GMCSF on the expression of 32,800 genes in a monocyte cell model (ML1 cells). Unexpectedly, the inventor found that there is a marked stimulation of chemokine release from monocyte cells. Surprisingly, the three genes with the greatest increases in expression were CXCL8, CCL2 and pro-PBP (see Table 2). The inventor repeated the microarray expression studies using PGE and GMCSF, and found a similar pattern of stimulation of chemokine release from monocyte cells. In this study each of CXCL8, CCL2 and pro-PBP were within the top eight genes with increased expression levels (Table 3). The increased expression of CXCL8, CCL2 and pro-PBP was confirmed by RT-PCR and protein release studies to result from the synergistic effect of PGE and GMCSF (see Example 1).

Table 2 also shows the relative lack of response to the cAMP elevating agent forskolin in combination with GMCSF (column 3 cf column 5). Thus, the increase in expression of CXCL8, CCL2 and PBP is not primarily due to an increase in intracellular cAMP and, therefore, appears to be the result of a different mechanism to that which causes an increase in expression of the pro-tolerant cytokine IL-10 (WO 2004/035083, WO 2005/044298).

The pattern of chemokine induction by PGE and GMCSF resembles the end of the first phase of wound repair and thus the inventor has realised in a rat model of wound healing, that the combination of PGE and GMCSF may be used to accelerate or promote wound repair. Without wishing to be bound by theory, the inventor believes that a PGE and GMCSF polarise monocytes into a pro-wound healing phenotype characterised by increased CXCL8; CCL2 and CXCL7 release. In addition, the effects of PGE and GMCSF are prolonged and continue after the removal of these agents, thus the cells are selectively differentiated.

In particular, slow healing wounds, such as those in areas of the skin that are poorly vascularised, could be accelerated or promoted by the local administration of PGE and GMCSF. Also, wounds in those patients, such as the elderly, who have a less-than-optimal ability to secrete cytokines such as CXCL8, CCL2 and CXCL7, thus not attracting leukocytes and depriving the wounded tissue of healing-inducing cytokines, would benefit from this treatment. Indeed there is an application for accelerating wound healing in a wider range of applications including skin wounds and surgical operation wounds in the otherwise healthy patient. It is also believed to be possible to accelerate or promote wound repair in the case of gastrointestinal damage such as that associated with ulcers or Crohn's disease.

As far as the inventor is aware, there has never been any suggestion that a combination of a PGE and GMCSF could be used to stimulate CXCL8, CCL2 and PBP-CXCL7 expression and/or release in monocytic cells, and there has been no suggestion of any treatment regime using this combination to stimulate CXCL8, CCL2 and PBP-CXCL7.

Furthermore, as far as the inventor is aware, there has never been any suggestion that the combination of a PGE and GMCSF might be therapeutically useful in wound healing.

In addition, the inventor has shown that the combination of PGE and GMCSF increases the expression of COX-2, CD14 and the calgranulins A and B in monocyte cells. COX-2 is believed to be involved in maintaining the pro-wound healing phenotype after removal of the PGE and GMCSF, while CD14 is a differentiation marker and is evidence of a more differentiated state. The calgranulins (S100 proteins) are also relevant to wound healing as they are natural antimicrobial agents, and a natural antimicrobial activity would greatly assist wound healing. Furthermore, the inventor now has provided evidence that the combination of PGE and GMCSF promotes the expression of genes involved in angiogenesis and Notch signalling, both of which are elements of the wound healing process.

A first aspect of the invention provides a method of promoting healing of a wound in a patient comprising administering to the patient (i) a prostaglandin E (PGE) or an agonist thereof and/or an agent which increases the local concentration, or effect of a PGE and (ii) granulocyte-macrophage colony stimulating factor (GMCSF) or a derivative thereof.

By "promoting healing of a wound" we mean that the PGE or agonist thereof or agent which increases the local concentration, or effect, of a PGE, and the GMCSF or derivative thereof provide a cytokine environment at the site of the wound that accelerates or promotes healing of the wound. In other words, the PGE or agonist thereof or agent that increases the local concentration, or effect, of PGE and the GMCSF or derivative thereof stimulate the release of cytokines such as CXCL8, CCL2 and CXCL7 that are necessary for the first phase of wound healing, thereby promoting healing of a wound. The first phase of wound healing lasts until approximately the fourth day. Therefore, by accelerating the healing of the wound within the first four days, wound healing would be promoted.

Furthermore, leukocytes attracted by the combination of the PGE or agonist thereof and the GMCSF or derivative thereof will also be further differentiated by the PGE-rich environment, leading to reduced or altered activation of neutrophils, which is advantageous for wound healing.

By a prostaglandin E (PGE) we mean prostaglandin $E_1$ ($PGE_1$) and prostaglandin $E_2$ ($PGE_2$). $PGE_2$ is more preferred. $PGE_2$ is commercially available, for example from Pharmacia and Upjohn as Prostin E2.

The PGE agonist may be, but need not be, a prostanoid which binds an EP receptor, such as the EP2 or EP4 receptor. Since the combination of GMCSF and forskolin, a stimulator of adenyl cyclase and the protein kinase A pathway, is quite inefficient at increasing the levels of the pro-wound healing cytokines shown in Table 2, the effect of PGE and GMCSF is not due to raised cAMP levels alone. Thus, the PGE or agonist thereof may not necessarily act via the EP2 or EP4 receptors, which are the receptors normally used by PGEs. Without being by bound by theory, the inventor believes that the PGE may be acting on more than one EP receptor at a time (including the EP 1, EP2 and EP4 receptors), or via a different prostaglandin receptor, or at the EP2 or EP4 receptors but via a different pathway.

By a PGE agonist we mean any compound which acts as a PGE agonist on a prostaglandin E receptor, such as the EP1, EP2, EP3 or EP4 receptors. It is preferred that the PGE agonist is an analogue of $PGE_2$. Synthetic analogues include those modified at position 15 or 16 by the addition of a methyl group or those where the hydroxyl has been transposed from position 15 to position 16. Preferred examples of analogues of PGE include 16,16-dimethyl PGE and 19-hydroxy PGE (both 19-OH $PGE_1$ and 19-OH $PGE_2$). For the avoidance of doubt, the term PGE includes naturally-occurring PGEs as well as synthetic PGE analogues.

Suitable PGEs or agonists thereof include dinoprostone (sold as Propess by Ferring in Europe and Forest in the USA; sold as Prostin E2 by Pharmacia), misoprostol (which is sold as Cytotec by Searle and Pharmacia), alprostadil (which is sold as Caverject by Pharmacia and Viridal by Schwarz and MUSE by AstraZeneca) and limaprost.

Misoprostol is a PGE analogue which has EP2 and EP3 agonist effects. Its chemical structure is (±) methyl 11α, 16-dihydroxy-16-methyl-9-oxoprost-13-enoate.

Suitable PGE agonists are described in EP 1 097 922 and EP 1 114 816, incorporated herein by reference. Other suitable PGE agonists may also include any of the 19-OH PGE analogues described in U.S. Pat. No. 4,127,612, incorporated herein by reference.

By an agent which increases the local concentration of PGE, we mean an agent that enhances the synthesis of PGE, for example by enzyme activation or by increasing the local concentration of PGE precursors, any agent which inhibits the catabolism of PGE, or an agent which serves to attract PGE to the wound site. By an agent which increases the effect of PGE we include an agent which increases the number of PGE receptors.

Suitable agents which enhance the synthesis of PGE include activators of cyclooxygenases 1 and 2 and activators of phospholipase which generates arachidonic acid—the precursor of all prostaglandins. Suitable agents which inhibit the catabolism of PGE include inhibitors of prostaglandin dehydrogenases (PGDHs). It is preferred that the agent is an inhibitor of PGDH. Suitable inhibitors of PGDH include epidermal growth factor (EGF) (Mann et al, 2006) and peroxisome proliferator-activated receptor (PPAR) agonists (Cho and Tai, 2002). The involvement of PPAR agonists in wound healing has recently been documented. Specifically, Pioglitazone has been shown to exhibit gastroprotective and ulcer healing properties (Brzozowski et al, 2005). In addition, EGF has been demonstrated to accelerate wound healing (Tanaka et al, 2005) and has been shown to enhance healing of diabetic foot ulcers (Hong et al, 2006).

By "GMCSF" we include the gene product of the human GMCSF gene and naturally occurring variants thereof. The nucleotide and the amino acid sequence of human GMCSF is found in Genbank Accession No. NM_000758, and in FIG. 1 (SEQ ID NOs: 1 and 2, respectively). Some naturally occurring variants of GMCSF are also listed in NM_000758. GMCSF is also known as colony stimulating factor 2 (CSF2).

The invention includes the use of a derivative of GMCSF that retains the biological activity of wild-type GMCSF, i.e. that stimulates the production of granulocytes and macrophages from their progenitor cells, and which, in the presence of PGE, synergistically causes monocytes to express CXCL-8 (IL-8).

By "derivative" of GMCSF we include a fragment, fusion or modification or analogue thereof, or a fusion or modification of a fragment thereof.

By "fragment" of GMCSF we mean any portion of the glycoprotein that stimulates the production of granulocytes and macrophages from their progenitor cells and which in the presence of PGE causes monocytes to express CXCL-8 (IL-8). Typically, the fragment has at least 30% of the activity of full length GMCSF. It is more preferred if the fragment has at least 50%, preferably at least 70% and more preferably at least 90% of the activity of full length GMCSF. Most preferably, the fragment has 100% or more of the activity of full length GMCSF.

The derivatives may be made using protein chemistry techniques for example using partial proteolysis (either exolytically or endolytically), or by de novo synthesis. Alternatively, the derivatives may be made by recombinant DNA technology. Suitable techniques for cloning, manipulation, modification and expression of nucleic acids, and purification of expressed proteins, are well known in the art and are described for example in Sambrook et al (2001) *"Molecular Cloning, a Laboratory Manual"*, 3$^{rd}$ edition, Sambrook et al (eds), Cold Spring Harbor Laboratory Press, Cold Spring Harbor, N.Y., USA, incorporated herein by reference.

The invention also includes modifications of full length GMCSF, or a fragment thereof, that stimulate the production of granulocytes and macrophages from their progenitor cells and which in the presence of PGE cause monocytes to express CXCL-8 (IL-8).

Such modifications include deglycosylating the glycoprotein either fully or partially. Other modifications include full length GMCSF, or a fragment thereof, having a different glycosylation pattern from that found in naturally occurring human GMCSF.

Other modifications of full length GMCSF, or a fragment thereof, include amino acid insertions, deletions and substitutions, either conservative or non-conservative, at one or more positions. Such modifications may be called analogues of GMCSF. By "conservative substitutions" is intended combinations such as Gly, Ala; Val, Ile, Leu; Asp, Glu; Asn, Gln; Ser, Thr; Lys, Arg; and Phe, Tyr. Such modifications may be made using the methods of protein engineering and site-directed mutagenesis, as described in Sambrook et al 2001, supra. Preferably, the modified GMCSF or modified GMCSF fragment retains at least 90% sequence identity with full length GMCSF, or the respective GMCSF fragment. More preferably, the modified GMCSF or modified GMCSF fragment has at least 91%, 92%, 93%, 94% or 95% sequence identity, and yet more preferably at least 96%, 97%, 98% or 99% sequence identity with full length GMCSF, or the respective GMCSF fragment. Preferably, the modified GMCSF or modified GMCSF fragment retains at least 30% of the activity of full length GMCSF. It is more preferred if the modified GMCSF or GMCSF derivative has at least 50%, preferably at least 70% and more preferably at least 90% of the activity of full length GMCSF. Most preferably, the modified GMCSF or modified GMCSF fragment has 100% or more of the activity of full length GMCSF.

The invention also includes the use of a fusion of full length GMCSF, or a fragment thereof, to another compound. Preferably, the fusion retains at least 30% of the activity of full length GMCSF. It is more preferred if the fusion has at least 50%, preferably at least 70% and more preferably at least 90% of the activity of full length GMCSF. Most preferably, the fusion has 100%, or more, of the activity of full length GMCSF.

GMCSF and analogues thereof are described in the following publications, each of which is incorporated herein by reference: U.S. Pat. No. 5,229,496 (Deeley et al); U.S. Pat. No. 5,391,485 (Deeley et al); U.S. Pat. No. 5,393,870 (Deeley et al); U.S. Pat. No. 5,602,007 (Dunn et al); Wong et al, 1985; Lee et al, 1985; Cantrell et al, 1985; and Miyatake et al, 1985.

While it is preferred that GMCSF is human GMCSF as defined above, by GMCSF we also include GMCSF from other species. It is appreciated that for applications in which GMCSF is administered to a non-human subject, the GMCSF is preferably from the same species as the subject. If the GMCSF is administered to a human subject, the GMCSF is preferably human GMCSF or a derivative thereof.

Suitable GMCSF for the practice of this invention can be obtained from Peprotech EC Ltd., 29 Margravine Road, London, W6 8LL, catalogue number 300-03.

A preferred GMCSF for the practice of this invention is sargramostim, the proper name for yeast-derived recombinant human GMCSF, sold under the trade name Leuidne® produced by Immunex, Inc. Leukine® is a recombinant human GMCSF produced in a *S. cerevisiae* expression system. Leukine® is a glycoprotein of 127 amino acids characterised by 3 primary molecular species having molecular masses of 19,500, 16,800 and 15,500 Daltons. The amino acid sequence of Leukine® differs from natural human GMCSF by a substitution of leucine at position 23, and the carbohydrate moiety may be different from the native protein. Leukine® is suitable for subcutaneous or intravenous administration (Leukine® Package Insert Approved Text, February 1998).

Another GMCSF suitable for the practice of this invention is molgramostim, the proper name for *E. coli*-derived recombinant human GMCSF, sold under the trade name Leucomax® (Schering-Plough). Leukomax® is a recombinant human GMCSF produced in an *E. coli* expression system. Leucomax® is a water soluble, non-glycosylated protein of 127 amino acids having a molecular mass of 14,477 Daltons. The amino acid sequence of Leucomax® differs from natural human GMCSF by a substitution of isoleucine at position 100. Leucomax® is available as a powder which, once reconstituted, is suitable for subcutaneous or intravenous administration (Leucomax® Data Sheet, November 2002).

A further GMCSF suitable for the practice of this invention is regramostim, the proper name for CHO-derived recombinant human GMCSF. Regramostim is a recombinant human GMCSF of 127 amino acids that is more highly glycosylated than sargramostim.

Typically, if the GMCSF or derivative thereof is produced recombinantly, it is purified away from the cells in which it is produced. Thus, in an embodiment of the invention, cells are not administered to the patient, i.e. there are no cells present in the therapeutic composition that is administered to promote healing of the wound.

It is preferred if the GMCSF or derivative thereof is administered to the patient as a polypeptide (whether or not glycoyslated). In a less preferred embodiment, the GMCSF or derivative thereof may be administered to the patient in the form of a polynucleotide that encodes the GMCSF or derivative thereof. Alternatively, the GMCSF or derivative thereof is not administered to the patient in the form of a polynucleotide that encodes the GMCSF or derivative thereof.

Unless the context indicates otherwise, wherever the term "GMCSF" is used, a derivative as herein defined is included.

Suitable doses of the PGE or agonist thereof to be administered typically range from 0.01 to 100 µg. Preferably, the amount of the PGE or agonist thereof ranges from 0.05 to 50 µg. Typically, amounts of 0.1 to 5 µg, or 5 to 20 µg, or 20 to 50 µg may be administered. Suitable doses of the agent which increases the local concentration or effect of PGE may be determined by the physical. Typically they would be in the range of 0.01 to 100 µg.

Suitable doses of the GMCSF or the derivative thereof to be administered typically range from 0.01 to 400 µg. Preferably, the amount of the GMCSF or the derivative thereof ranges from 0.05 µg to 200 µg. Typically, amounts of 0.1 to 5 µg, or 5 to 50 µg, or 50 to 200 µg may be administered.

Preferably, one or both of the PGE or agonist thereof or agent which increases the local concentration or effect of PGE and the GMCSF or derivative thereof are administered locally to the patient at the site of the wound. Most preferably, both the PGE or agonist thereof and the GMCSF or derivative thereof are administered locally to the patient at the site of the wound.

In a preferred embodiment, the wound to be treated is a sterile wound, i.e. the wound is not infected. If the wound is infected, the wound may be sterilised, for example by the administration of an antimicrobial agent. Clearly, however, the use of an antimicrobial agent would also serve to prevent infection of a sterile wound being treated.

Thus, typically, the method may further comprise administering an antimicrobial agent to the patient. In an embodiment, the antimicrobial agent is administered locally to the patient at the site of the wound. Suitable antimicrobial agents include antibacterial agents, antifungal agents and antiviral agents, as is well known to the person of skill in the art. Antibacterial agents include, for example natural and synthetic penicillins and cephalosporins, sulphonamides, erythromycin, kanamycin, azithromycin, clarithromycin, roxithromycin, tetracycline, oxytetracycline, chloramphenicol, rifanpicin, and including gentamicin, ampicillin, benzypenicillin, benethamine penicillin, benzathine penicillin, phenethicillin, phenoxy-methyl penicillin, procaine penicillin, cloxacillin, flucloxacillin, methicillin sodium, amoxicillin, bacampicillin hydrochloride, ciclacillin, mezlocillin, pivampicillin, talampicillin hydrochloride, carfecillin sodium, piperacillin, ticarcillin, mecillinam, pirnecillinan, cefaclor, cefadroxil, cefotaxime, cefoxitin, cefsulodin sodium, ceftazidime, ceftizoxime, cefuroxime, cephalexin, cephalothin, cephamandole, cephazolin, cephradine, cefurome, latamoxef disodium, aztreonam, glycylcyclines, chortetracycliie hydrochloride, clomocycline sodium, demeclocydine hydrochloride, doxycychne, lymecycline, minocycline, oxytetracycline, amikacin, framycetin sulphate, neomycin sulphate, netilmicin, tobramycin, colistin, sodium fusidate, fupirocin, polymyxin B sulphate, spectinomycin, vancomycin, teicoplanin, calcium sulphaloxate, sulphametopyrazine, sulphadiazine, sulphadimidine, sulphaguanidine, sulphaurea, capreomycin, metronidazole, timidazole, cinoxacin, ciprofloxacin, norfloxacin, nitrofurantoin, hexamine, streptomycin, carbenicillin, colistimethate, polymyxin B, furazolidone, nalidixic acid, trimethoprim-sulphamethoxazole, clindamycin, lincomycin, cycloserine, isoniazid, ethambutol, ethionamide, pyrazinamide, meropenem and imipenem and the like; antifungal agents include, for example miconazole, ketoconazole, itraconazole, fluconazole, amphotericin, flucytosine, griseofulvin, natamycin, nystatin, and the like; and antiviral agents include agents such as acyclovir, AZT, ddI, amantadine hydrochloride, inosine pranobex, vidarabine, and the like.

The method may also include administering an analgesic agent or an anesthetic agent locally to the patient at the site of the wound. Suitable analgesic agents include methylsalicylate, salicylic acid, dyclonine and aloe vera. Suitable local anesthetic agents include benzocaine, lidocaine, xylocaine or butamben picrate.

In a preferred embodiment, the PGE or agonist thereof or agent which increases the local concentration or effect of PGE and the GMCSF or derivative thereof, together with any of the other optional active agents described herein, are administered as a pharmaceutical composition containing a pharmaceutically acceptable carrier, diluent or excipient (including combinations thereof). The carrier, diluent or excipient must be "acceptable" in the sense of being compatible with the active agents of the invention and not deleterious to the recipients thereof. Typically, the carriers will be water or saline which will be sterile and pyrogen free. Acceptable carriers or diluents for therapeutic use are well known in the pharmaceutical art, and are described, for example, in Remington's Pharmaceutical Sciences, Mack Publishing Co. (*Remington: The Science and Practice of Pharmacy* $21^{st}$ Edition, 2005, ISBN: 0-7817-4673-6). The choice of pharmaceutical carrier, excipient or diluent can be selected with regard to the intended route of administration and standard pharmaceutical practice.

The pharmaceutical compositions may comprise as, or in addition to, the carrier, excipient or diluent any suitable binder(s), lubricant(s), suspending agent(s), coating agent(s), or solubilising agent(s). Preservatives, stabilisers, dyes and even flavoring agents may be provided in the pharmaceutical composition. Examples of preservatives include sodium benzoate, sorbic acid and esters of p-hydroxybenzoic acid. Antioxidants and suspending agents may be also used.

Typically, the method may be used for promoting the healing of an external wound.

In this embodiment, the method may further comprise administering a skin permeability enhancer locally to the patient at the site of the wound. By a skin permeability enhancer we mean a dispersion agent or an agent which allows for increased transdermal transfer, delivery or penetration of the active agent(s). Suitable skin permeability enhancers such a dimethyl sulphoxide (DMSO) and the like. Suitable enhancers are ones which are compatible with the PGE or agonist thereof and/or the GMCSF or derivative thereof (e.g. are solvents thereof).

In an embodiment of the invention, the PGE or agonist thereof or agent which increases the local concentration or effect of PGE and the GMCSF or derivative thereof, and optionally the antimicrobial agent and/or the analgesic agent and/or the anesthetic agent and/or the skin permeability enhancer, are administered as the sole active agents for promoting the healing of the wound In general, any or all of the above active agents (i.e., the PGE or agonist thereof or agent which increases the local concentration or effect of PGE, the GMCSF or derivative thereof, and the optional skin permeability enhancer, antimicrobial agent, analgesic agent and anesthetic agent) may be administered topically for wound treatment and for promoting healthy skin development. The active agents may be administered topically by any means either directly or indirectly to the selected tissue as a spray, foam, powder, lotion, cream, gel, paste or solution. The terms lotion, cream, gel and paste include viscous spreadable compositions and ointments such as are often applied directly to the skin or spread onto a bandage or wound dressing material. The active agents may be covalently attached, stably adsorbed or otherwise applied to a skin covering or wound dressing material. To facilitate healing after surgery, the active agents may be the applied directly to target tissues or to prosthetic devices. The compositions can be administered by aerosol, as a foam or as a mist along with other agents directly onto the skin or wound.

Suitable concentrations of the PGE or agonist thereof in the pharmaceutical formulation typically range from 0.01 to 100 µg/ml. Preferably, the concentration of the PGE or agonist thereof ranges from 0.05 to 50 µg/ml. More preferably, concentrations of 0.1 to 1 µg/ml, or 1 to 10 µg/ml, or 10 to 20 µg/ml may be employed. Suitable concentrations of the agent that increases the local concentration or effect of PGE would typically range from 0.01 to 100 µg/ml.

Suitable concentrations of the GMCSF or the derivative thereof in the pharmaceutical formulation typically range from 0.01 to 50 µg/ml. Preferably, the concentration of the GMCSF or the derivative thereof ranges from 0.05 to 25 µg/ml. More preferably, concentrations of 0.1 to 1 µg/ml, or 1 to 10 µg/ml, or 10 to 20 µg/ml may be employed.

The pharmaceutical preparation of sprays, foams, powders, lotions, creams, gels, pastes and solutions is very well known in the art (see, for example, *Remington: The Science and Practice of Pharmacy* 21$^{st}$ Edition, 2005, ISBN: 0-7817-4673-6).

U.S. Pat. No. 6,251,423 (Smith & Nephew) describes a suitable sterilisable paste or cream formulation which can be topically applied to a patient, or applied to a surface of a bandage or wound dressing.

Suitable wound dressings are very well known in the art, and some are described, for example, in U.S. Pat. Nos. 6,191,335; 5,792,089; 5,662,924 and 4,460,369 (Smith & Nephew), each of which is incorporated by reference. Wound dressings are reviewed, for example, by Harvey 2005; Vermeulen et al, 2005; Menaker, 2004; and Lionelli & Lawrence (2003), each of which is incorporated by reference.

In another embodiment, the PGE or agonist thereof or agent which increases the local concentration or effect of PGE, GMCSF or a derivative thereof, together with any of the other optional active agents, may be administered as components of a tissue sealant such a fibrin glue. Fibrin glues generally are prepared from: (1) a fibrinogen concentrate, which contains fibronectin, Factor XIII, and von Willebrand factor; (2) dried human or bovine thrombin; and (3) calcium ions. Commercially prepared fibrin glues may often contain bovine components. The fibrinogen concentrate can be prepared from plasma by cryoprecipitation followed by fractionation, to yield a composition that forms a sealant or clot upon mixture with thrombin and an activator of thrombin such as calcium ions. The fibrinogen and thrombin concentrates are prepared in lyophilised form and are mixed with a solution of calcium chloride immediately prior to use. Upon mixing, the components are applied to a tissue where they coagulate on the tissue surface and form a clot that includes cross-linked fibrin, thus maintaining the PGE or agonist thereof and the GMCSF or a derivative thereof, at the site of the wound. Suitable tissue sealant compositions, including fibrin glues and supplemented fibrin glues, are very well known in the art, and are reviewed by Spotnitz & Prabhu (2005), MacGillivray (2003), Clark (2003), and Albala (2003), each of which is incorporated by reference.

In another embodiment, any one or more of the active agents may be administered in an implantable device that delivers the active agent(s) to the wound, typically for controlled release of the active agent. Suitable implantable devices are known in the art and are described, for example, in US Patent Application No. 2004/0034357 (Smith & Nephew). The active agents, especially the PGE or agonist thereof and the GMCSF or a derivative thereof could be included in microspheres, and administered for contemporaneous controlled release of the active agents.

In a still further embodiment, any one or more of the active agents is administered by injection.

Preferably, any two or more of the active agents are administered simultaneously.

Also preferably, the PGE or agonist thereof or agent which increases the local concentration or effect of PGE and the GMCSF or a derivative thereof are administered by the same route.

It is appreciated that the method may also be used for promoting the healing of an internal surgical wound. However, unlike other forms of wound healing treatment, the method may be helpful in providing a pro-healing environment before a wound is present. Thus, the method may be useful in providing a localised pro-wound healing environment in patients who are about to undergo surgery. It may be further beneficial to continue the administration during or after completion of the surgery.

Whether or not a particular patient is one who is expected to benefit from treatment may be determined by the physician.

It is appreciated that the method may also be useful for combating an ulcer or gastrointestinal damage, such as that associated with Crohn's disease. By "combating" a particular disease or condition we include the meaning of treating, preventing or ameliorating the symptoms of that particular disease or condition.

In such an embodiment, one or both of the PGE or agonist thereof or agent which increases the local concentration or effect of PGE and the GMCSF or derivative thereof, may be administered orally, especially in a controlled release formulation. Alternatively, one or both of the PGE or agonist thereof or agent which increases the local concentration or effect of PGE and the GMCSF or derivative thereof, may be administered as a suppository or capsule. The suppository or capsule may have an enteric coating for release of the active agent in the bowel of the patient.

Pregnancy may be a contraindication for the present invention. In fact, pregnancy is a contraindication for several prostaglandins including misoprostol. Cytotec (misoprostol) does not cause hypotension, but this may be a possible risk with the method of the invention.

In a particular embodiment, the invention does not include administering a stem cell, such as a skin stem cell, to the patient.

In another particular embodiment, the invention does not include administering the PGE or agonist thereof and the GMCSF or derivative thereof in the form of a solid substrate comprising a collagen matrix containing a plurality of vertebrate cells that are genetically engineered to express GMCSF; $PGE_1$ or $PGE_2$ associated with the solid substrate; and a plurality of microcarriers.

In another particular embodiment, the invention does not include administering the PGE or agonist thereof and the GMCSF or derivative thereof in the form of a composition comprising a plurality of vertebrate cells that are genetically engineered to express GMCSF; a plurality of microcarriers; and $PGE_1$ or $PGE_2$.

A second aspect of the invention provides the use of (i) a PGE or an agonist thereof and/or an agent which increases the local concentration or effect of PGE, and (ii) GMCSF or a derivative thereof, in the preparation of a medicament for promoting healing of a wound in a patient. Thus, the PGE or agonist thereof and/or agent which increases the local concentration or effect of PGE and the GMCSF or derivative thereof may be combined in the same medicament before administration to the patient.

A third aspect of the invention provides the use of GMCSF or a derivative thereof in the preparation of a medicament for promoting healing of a wound in a patient who is administered a PGE or an agonist thereof and/or an agent which increases the local concentration or effect of PGE. Thus, the patient may already have been administered the PGE or agonist thereof and/or the agent which increases the local concentration or effect of PGE before administration of the GMCSF or derivative thereof, or is administered the PGE or agonist thereof and/or the agent which increases the local concentration or effect of PGE at the same time as the GMCSF or derivative thereof, or will be administered the PGE or agonist thereof and/or the agent which increases the local concentration or effect of PGE after administration of the GMCSF or derivative thereof.

A fourth aspect of the invention provides the use of a PGE or an agonist thereof and/or an agent which increases the local concentration or effect of PGE in the preparation of a medicament for promoting healing of a wound in a patient who is administered GMCSF or a derivative thereof. Thus, the patient may already have been administered the GMCSF or derivative thereof before administration of the PGE or agonist thereof and/or the agent which increases the local concentration or effect of PGE, or is administered the GMCSF or derivative thereof at the same tine as the PGE or agonist thereof and/or the agent which increases the local concentration or effect of PGE, or will be administered the GMCSF or derivative thereof after administration of the PGE or agonist thereof and/or the agent which increases the local concentration or effect of PGE.

Preferences for the PGE, the agonist thereof and the agent which increases the local concentration or effect of PGE, and for the GMCSF and the derivative thereof, routes of administration, doses and so on for the second, third and fourth aspects of the invention are as defined above with respect to the first aspect of the invention.

It is appreciated that the medicaments described above in the second, third and fourth aspects of the invention may also comprise a skin permeability enhancer, an antimicrobial agent, an analgesic agent and/or an anesthetic agent. It is further appreciated that the medicaments described above in the second, third, and fourth aspects of the invention may be for promoting healing of a wound in a patient who has been administered a skin permeability enhancer, an antimicrobial agent, an analgesic agent and/or an anesthetic agent. The preferences for the skin permeability enhancer, antimicrobial agent, analgesic agent and the anesthetic agent are the same as described above for the first aspect of the invention.

Preferably, the medicament of the second, third and fourth aspects of the invention is formulated for local administration to the patient at the site of the wound. The medicament may be formulated in the form of a gel, cream, lotion, paste, patch or spray as described above. Alternatively, the medicament may be formulated in the form of a wound dressing, bandage or tissue sealant as described above. As a further alternative, the medicament may be formulated for administration by injection.

The medicament may be suitable for promoting the healing of an external wound or an internal surgical wound The medicament may also be suitable for promoting the healing of an internal wound such as an ulcer or a wound associated with Crohn's disease. Thus the invention includes the use of (i) PGE or an agonist thereof and/or an agent which increases the local concentration or effect of PGE and (ii) GMCSF or a derivative thereof as defined in the second, third and fourth aspects of the invention, and optionally any of the other active agents mentioned above, in the preparation of a medicament for combating an ulcer or for combating Crohn's disease. In this embodiment, the medicament may be formulated for oral administration, or as a suppository or capsule, as described above.

A fifth aspect of the invention provides a wound dressing, bandage or tissue sealant composition comprising (i) a PGE or an agonist thereof and/or an agent which increases the local concentration or effect of PGE and (ii) GMCSF or a derivative thereof.

Preferences for the PGE or agonist thereof, the agent which increases the local concentration or effect of PGE, and the GMCSF or derivative thereof, are as defined above with respect to the first aspect of the invention.

In an embodiment, the wound dressing, bandage or tissue sealant composition further comprises any one or more of a skin permeability enhancer, an antimicrobial agent, an analgesic agent or an anesthetic agent. Preferences for the skin permeability enhancer, the antimicrobial agent, the analgesic agent and the anesthetic agent are as defined above with respect to the first aspect of the invention.

Typically, the wound dressing, bandage or tissue sealant composition is suitable for application to an external wound, as discussed above. In another embodiment, the wound dressing or tissue sealant composition may be suitable for application to an internal surgical wound, as discussed above.

A sixth aspect of the invention provides a gel, cream, lotion, paste or spray comprising (i) a PGE or an agonist thereof and/or an agent which increases the local concentration or effect of PGE, (ii) GMCSF or a derivative thereof, and (iii) at least one further agent selected from an antimicrobial agent, an analgesic agent and an anesthetic agent.

Preferences for the PGE or agonist thereof, the agent which increases the local concentration or effect of PGE, the GMCSF or derivative thereof, the antimicrobial agent, the analgesic agent and the anesthetic agent are as defined above with respect to the first aspect of the invention.

In an embodiment, the gel, cream, lotion, paste or spray comprises any two or more of the antimicrobial agent, analgesic agent and anesthetic agent.

In an embodiment, the gel, cream, lotion, paste or spray further comprises a skin permeability enhancer as defined above with respect to the first aspect of the invention.

Typically, the gel, cream, lotion, paste or spray is suitable for application to an external wound. In another embodiment, the gel, cream or lotion may be suitable for application to an internal surgical wound.

The inventor has shown that PGE and GMCSF cause enhanced expression of CXCL8, CCL2 and PBP-CXCL7 in cells of the macrophage/monocyte lineage. By "cells of the macrophage/monocyte lineage" we include cells that are derived from monocyte precursors and include macrophages and monocytes.

A seventh aspect of the invention provides a method of stimulating or enhancing expression of CXCL8, CCL2 and PBP in cells of the macrophage/monocyte lineage, the method comprising administering to the cells (i) a PGE or agonist thereof and/or an agent which increases the local concentration or effect of PGE and (ii) GMCSF or a derivative thereof.

The invention also includes a method of stimulating or enhancing secretion of CXCL8, CCL2 and CXCL7 from cells of the macrophage/monocyte lineage by administering to the cells (i) a PGE or agonist thereof and/or an agent which increases the local concentration or effect of PGE and (ii) GMCSF or a derivative thereof.

The method may be performed in vitro or ex vivo. Alternatively, the method may be performed in vivo.

This aspect of the invention includes the use of (i) a PGE or agonist thereof and/or an agent which increases the local concentration or effect of PGE and (ii) GMCSF or a derivative thereof in the preparation of a medicament for stimulating or enhancing expression of CXCL8, CCL2 and PBP in cells of the macrophage/monocyte lineage.

Similarly, the invention includes the use of (i) a PGE or agonist thereof and/or an agent which increases the local concentration or effect of PGE and (ii) GMCSF or a derivative thereof in the preparation of a medicament for stimulating or enhancing secretion of CXCL8, CCL2 and CXCL7 from cells of the macrophage/monocyte lineage.

All of the documents referred to herein are incorporated herein, in their entirety, by reference.

The listing or discussion of a prior-published document in this specification should not necessarily be taken as an acknowledgement that the document is part of the state of the art or is common general knowledge.

The invention will now be described in more detail with the aid of the following Figures and Examples.

FIG. 1 cDNA and amino acid sequence (FIGS. 1A (SEQ ID No 1) and 1B (SEQ ID No 2), respectively) of human GMCSF, taken from Genbank Accession No. NM_000758.

FIG. 2 is a Venn diagram showing the overlap in differentially expressed genes between treatments GMCSF+PGE [treatment 1] and control (group 2-group 1), GMCSF+HSP [treatment 2] and control (group 3-group 1) and GMCSF+HSP [treatment 2] and GMCSF+PGE [treatment 1] (group 3-group 2).

Figure 5:
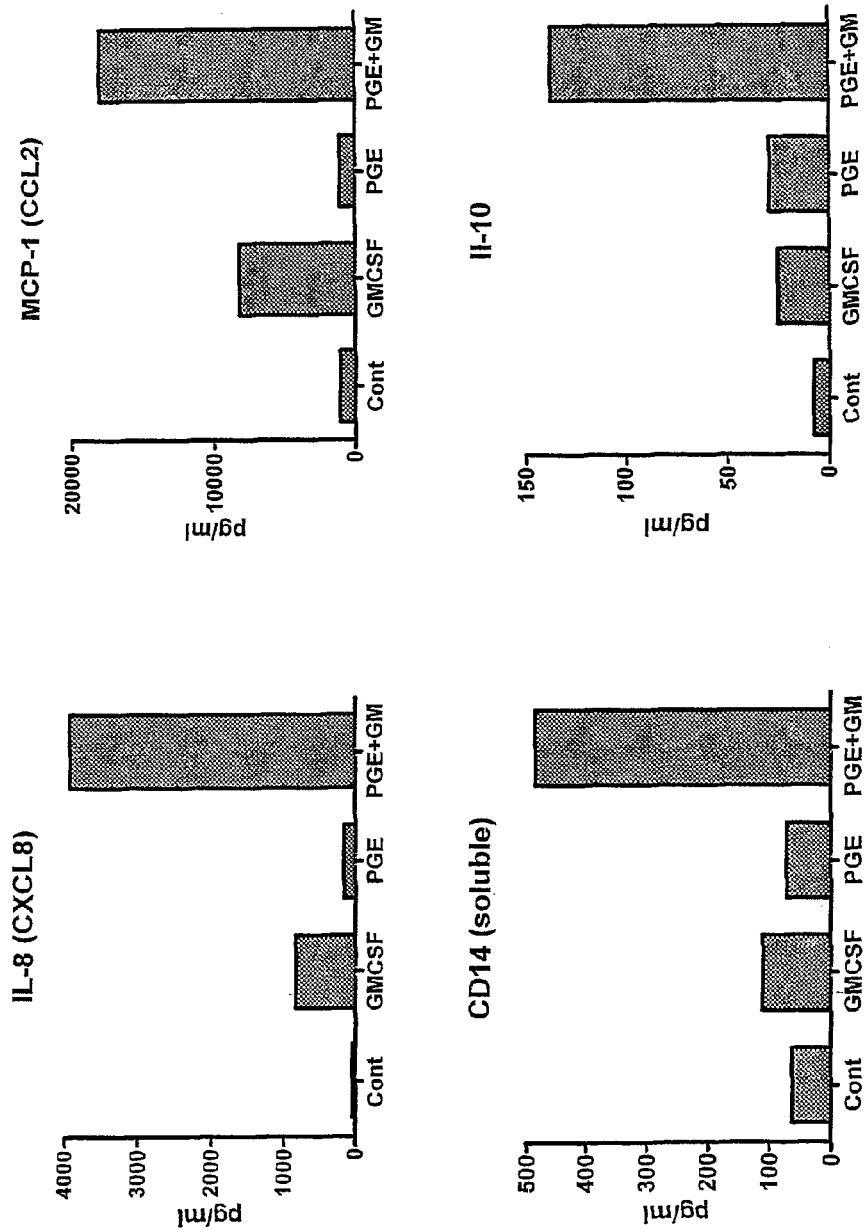

FIG. 5 is a graph showing the synergistic action of PGE and GMCSF on chemokine/protein release from monocytic U937 cells after 48 hours in culture. The release of chemokines CXCL8 and CCL2 in response to GMCSF and PGE demonstrates that the synergistic effect of GMCSF with human seminal plasma is reproduced by PGE. GMCSF and PGE also have a synergistic effect on the release of soluble CD14 and IL-10.

Figure 6:
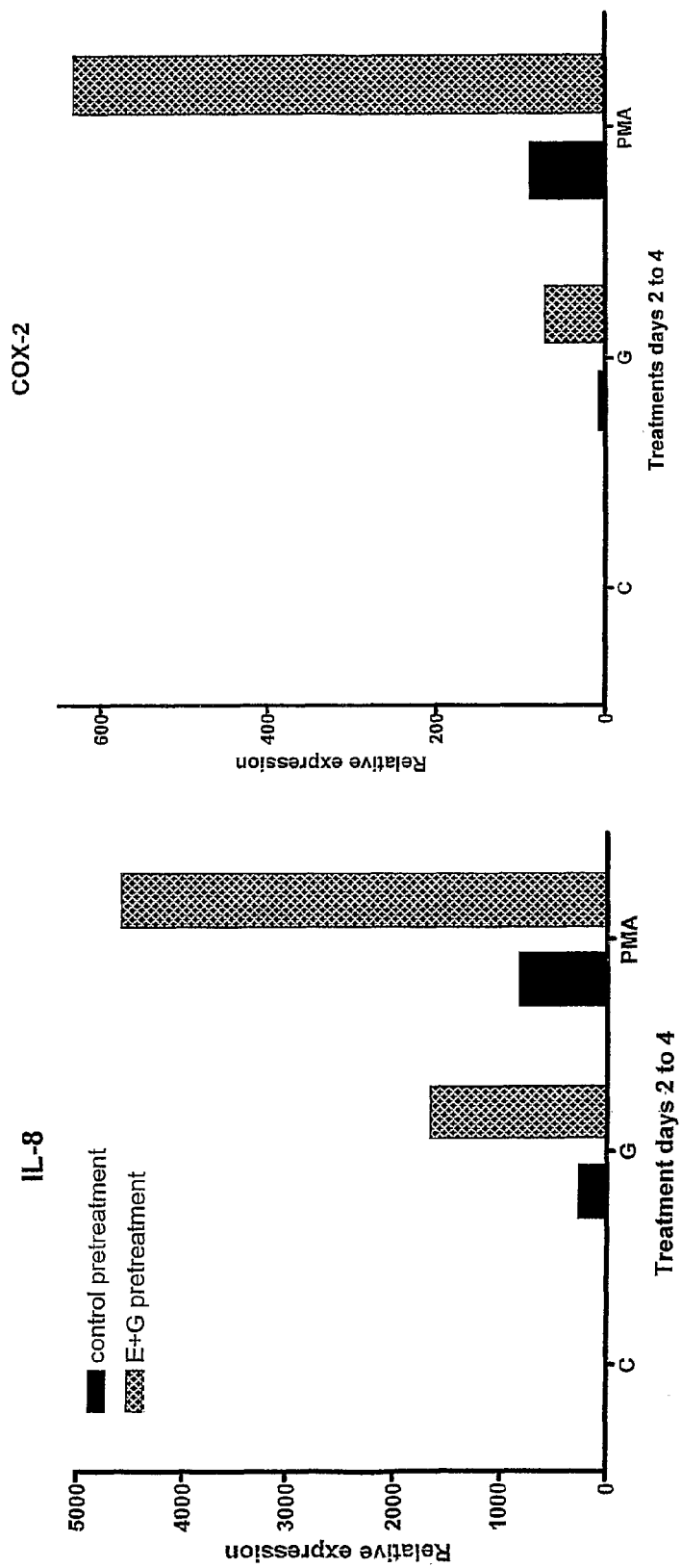

FIG. 6 is a graph showing the effect of pretreatment with PGE and GMCSF on IL-8 and COX-2 expression in ML1 cells. Cells were incubated for 48 hours either with no additions or with PGE together with GMCSF. The pre-treatments were removed and the cells were washed and then three further treatments were added: control, PGE and GMCSF, and Phorbol myristoyl acetate (PMA, which is a well established differentiation agent for monocytes). Incubation was continued for a further 48 hours. The effect of the PGE and GMCSF pretreatment is preserved at the end of the 4 day period after exposure to PMA.

Figure 7:
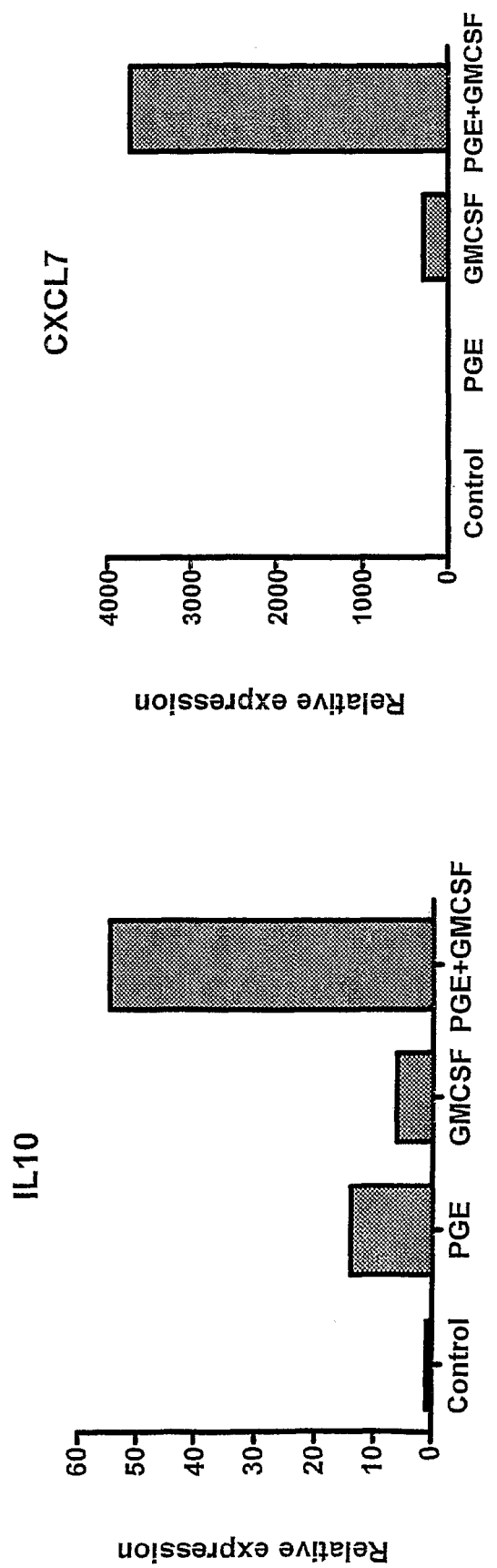

FIG. 7 is a graph showing the synergistic action of PGE and GMCSF on the expression of the pro-platelet basic protein (PBP) gene (referred to as CXCL7) in monocytic ML1 cells after 48 hours in culture. The expression of pro-PBP in response to GMCSF and PGE demonstrates that the effect seen in the expression arrays represents true synergism. Pro-PBP expression in response to GMCSF and PGE was increased 3725 times over the control. GMCSF and PGE were also shown to have a synergistic effect on the expression of IL-10, but to a lesser extent than for pro-PBP.

Figure 8:
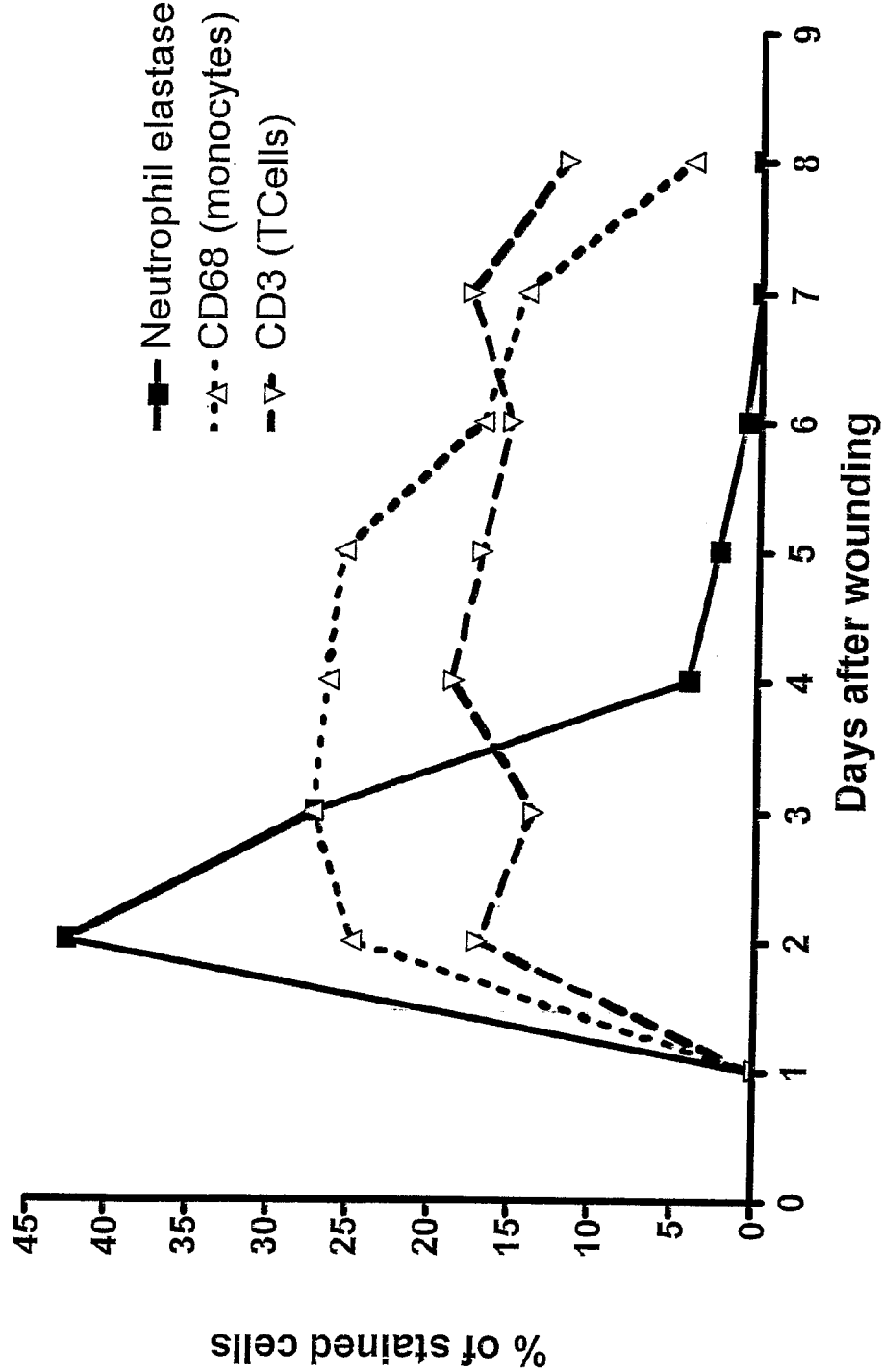

FIG. 8 is a graph derived from Engelhardt et al (1998) showing the arrival of both neutrophils and monocytes as a feature of wound repair in human wounds.

Figure 9:
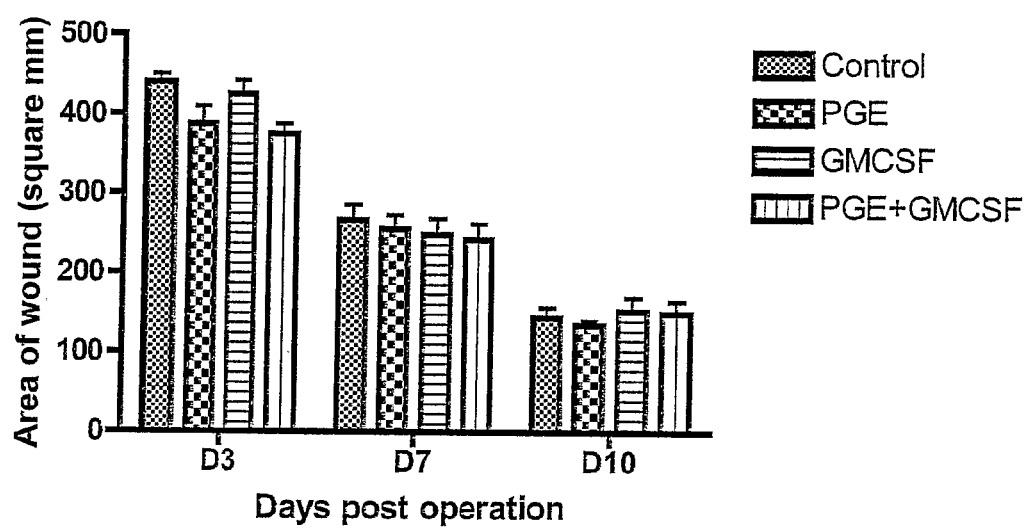

FIG. 9 is a graph showing wound area measurements in a rat model of wound healing, administered four different treatments, on days 3, 7 and 10 post surgery.

Figure 10:
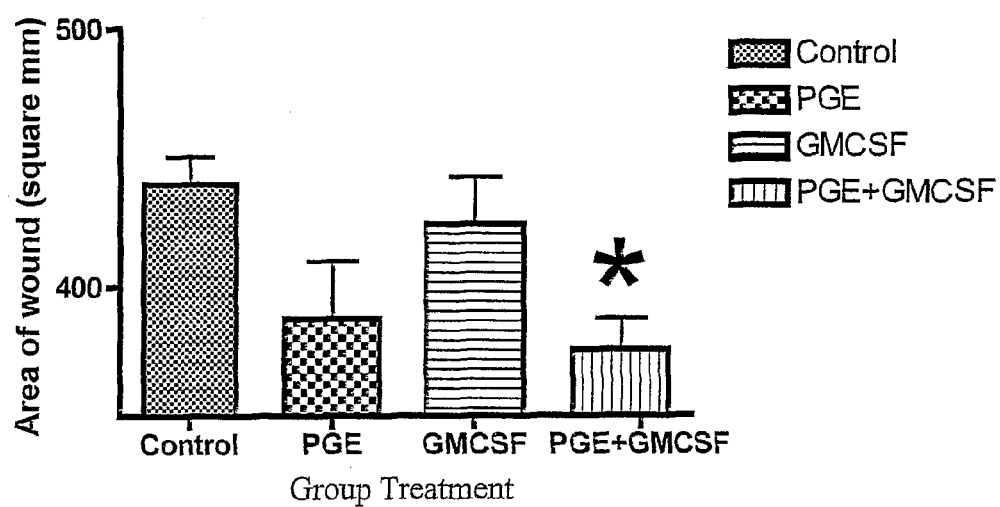

FIG. 10 is a graph showing wound area measurements in a rat model of wound healing, administered four different treatments, on day 3 post surgery. The asterisk denotes a significant decrease in wound area in rats treated with a combination of PGE and GMCSF, relative to control treated rats. No significant decrease was observed in rats administered either PGE or GMCSF alone.

FIG. 11 is a grid showing daily colour observations of wounds in rats administered each of the four treatments. Wounds were scored as being either red (R) brown (B) black or scab yellow (Y), whereby red indicates a less healed wound than brown. The grid shows the effect of PGE and GMCSF (treatment 4) on days 9 and 10, there being more brown scores than in control rats (treatment 1) or in rats administered either PGE or GMCSF alone (treatments 2 and 3).

EXAMPLE 1

Prostaglandin E/GMCSF Synergy on Cytokine Induction

Summary

Results from gene expression array studies using human seminal plasma (HSP) and GMCSF, and PGE and GMCSF, in a human monocyte model system showed an unexpected pattern of cytokine gene expression. In the first assay using a HSP/GMCSF treatment regime, a thousand-fold increase in the expression of several chemokines (chemotactic cytokines) was seen and the three mRNAs most highly increased over control were chemokines. The chemokine expression appeared to be cAMP independent. In the second assay using HSP/GMCSF and PGE/GMCSF treatment regimes, a several hundred-fold increase in the expression of several chemokines was seen. Four of the eight mRNAs most highly increased over control were chemokines, including the top three in the first assay. The chemokine pattern in response to HSP/GMCSF and PGE/GMCSF was very similar to that seen in the first phase of wound healing. These results suggest that an intervention of locally applied PGE, or an agent which increases its local concentration, and GMCSF may be therapeutically useful in wound healing Experimental Details Gene Expression Arrays U937 or ML1 (human monocyte cell lines) cells were grown in RPMI (PAA Laboratories) medium with 10% fetal calf serum added (PAA Laboratories). For the first assay, cells were treated with no additions, sterile-filtered (0.22 µM) 1% human seminal plasma (HSP) or forskolin (25 µM) with GMCSF at 5 ng/ml for 48 hours (results are shown in Table 2). The second set of arrays differs in the replicates. This second assay included 2 duplicate control cultures, 2 cultures treated with $10^{-6}$ M PGE+5 ng/ml GMCSF, and 4 treated with 1% HSP+5 ng/ml GMCSF. (The results in Table 3 are means of the replicates.)

Cells were pelleted and the mRNA was extracted with Tri reagent (Sigma, Poole, UK). Total RNA was obtained by addition of chloroform and subsequent isopropanol precipitation. Samples were analysed using ABI/Celera arrays consisting of 32,800 genes.

The concentration and quality of the total RNA was assessed by spectrophotometry (nanodrop) and bioanalyser (Agilent). RT-IVT was then carried out in accordance to the Applied Biosystems Chemiluminescent RT-IVT nanoamp (one-cycle) labeling protocol for all samples. QC procedures (Nanodrop and Agilent bioanalyser) were carried out on the cRNA samples to confirm the quality and quantity of the cRNA. The samples were fragmented and subsequently prepared for hybridisation to Applied Biosystems Human Genome Survey Microarray (Version 2), for 16 hours. Following hybridisation, the arrays were stained and washed using the Applied Biosystems Chemiluminescence detection kit. The arrays were finally scanned using the Applied Biosystems 1700 Chemiluminescent Microarray Analyzer. Array studies were carried out by MRC Gene-services, Cambridge, UK.

In the first assay, expressed genes (signal from treated cells divided by signal from control cells) were ranked and the 32 most highly expressed genes are listed in Table 2. In the second assay, expressed genes were ranked (signal from treated cells divided by signal from control cells), and the 32 most highly expressed genes are listed in Table 3. The second assay underwent statistical analysis and the genes were ranked according to the probability of being enhanced over control (as specified by the B value, which equals the log [base 2] of odds that a gene is differentially expressed). Only genes having a B value over 4 are listed in Tables 5 and 6. The gene expression is ranked by the increase in gene expression (log [Base 2] increase is shown as 'M'. The pathways in which the differentially expressed genes have been implicated are also listed in Table 7. The pathway analysis was performed using a proprietary programme by Geneservice Ltd (Cambridge UK).

RT-PCR for Measuring Cytokine Expression

High ranking genes were studied further by quantitative reverse transcription polymer chain reaction (RT-PCR) using the ABI Taqman system. Probes and primers for amplification and detection of IL-8 and a number of other molecules were designed using Primer Express (Applied Biosystems). In these studies, incubation of cells was identical to above and the effect of pure PGE was determined and found to be the same as that seen with human seminal plasma.

mRNA for specific genes was amplified in a Taqman 7700 machine for 40 cycles using FAM/TAMRA dyes on the probe. The Applied Biosystems kit was used to amplify and detect ribosomal (18S) RNA (using VIC/TAMRA dyes) as an internal control in the same reaction tube. After 40 cycles the Ct (related to cycle number at which signal appears) for the FAM and the 18S (VIC) were recorded and relative quantitation was achieved using the formula $2^{-\Delta\Delta Ct}$ where $\Delta$ refers to the difference between the FAM and VIC signal related to a standard comparator included in each run.

The primers used were as follows:

Pro-PBP (CXCL7) Accession number NM_002704

```
                                            (SEQ ID NO: 3)
Forward:    5'-CCAAAAACATCCAAAGTTTGGAA-3'

(SEQ ID NO: 4)
Reverse:    5'-CAGTGTGGCTATCACTTCGACTTG-3'

(SEQ ID NO: 5)
Probe:      5'-TGATCGGGAAAGGAACCCATTGCA-3'
```

COX-2 (Accession No. D28235)

```
                                            (SEQ ID NO: 6)
Forward:    5'-GTGTTGACATCCAGATCACATTTGA-3'

(SEQ ID NO: 7)
Reverse:    5'-GAGAAGGCTTCCCAGCTTTTGTA-3'

(SEQ ID NO: 8)
Probe:      5'-TGACAGTCCACCAACTTACAATGCTGACTATGG-3'
```

CXCL8 (CCL8, IL-8 (Accession No. NM_000584)

```
                                            (SEQ ID NO: 9)
Forward:    5'-CTGGCCGTGGCTCTCTTG-3'

(SEQ ID NO: 10)
Reverse:    5'-TTAGCACTCCTTGGCAAAACTG-3'

(SEQ ID NO: 11)
Probe:      5'-CCTTCCTGATTTCTGCAGCTCTGTGTGAA-3'

IL-10
                                            (SEQ ID NO: 12)
Forward:    5'-CTACGGCGCTGTCATCGAT-3'

(SEQ ID NO: 13)
Reverse:    5'-TGGAGCTTATTAAAGGCATTCTTCA-3'

(SEQ ID NO: 14)
Probe:      5'-CTTCCCTGTGAAAACAAGAGCAAGGCC-3'
```

ELISA for Measuring Cytokine Release

Medium was removed from cells and analysed by ELISA. A monoclonal capture antibody was coated onto 96 well plates and culture medium was added each well. A standard curve was created with recombinant protein. After incubation and washing, a biotin-labelled monoclonal antibody was added. Following further incubation and washing, peroxidase-labelled streptavidin was added. After washing, a tetramethyl benzidine substrate was added and colour developed in proportion to the concentration of the cytokine in the original sample/standard. Colour was read using a plate photometer (Labsystems, Multiskan).

Paired antibodies and recombinant standards for CD14, CXCL8 (IL-8), and CCL2 (MCP-1) were obtained from R&D Systems Ltd, Abingdon UK and antibodies for IL-10 were obtained from Pharmingen (BD Bioscience, Erembodegem, Belgium), as shown below in Table 1.

TABLE 1

| Analyte | Capture antibody | Detection antibody | Recombinant Standard |
|---|---|---|---|
| CD14 | MAB3833 | BAF383 | 383-CD-050 |
| IL8 (CXCL8) | MAB208 | BAF208 | 208-IL |
| MCP-1 (CCL2) | MAB679 | BAF279 | 279MC |
| IL10 | Pharmingen - 554497 | Pharmingen - 554499 | (Pharmingen) - 554611 |

Results

Table 2 shows the 32 genes with the highest level of increased expression relative to control. The $3^{rd}$ column is control expression levels; the $4^{th}$ column is the expression level after treatment with HSP and GMCSF; and the $5^{th}$ column is a ratio of columns 4 to 3. The chemokines are shown in bold.

The data in Table 3 shows that although the pattern of genes stimulated by PGE+GMCSF is slightly different from those stimulated by HSP+GMCSF, there is still a predominance of chemokine stimulation. 10 chemokines are ranked in the top 29 genes ranked by signal intensity of PGE+GMCSF (column 4) over control (column 3). The chemokines PBP-CXCL7, CCL2 and CXCL8 are all in the top 8.

Considering that these results are derived from expression studies on 32,000 genes using different batches of ML1 cells, and different treatment regimes, there is a very high correlation between the expression induced by PGE+GM-CSF (Table 3) compared to HSP+GMCSF (Table 2).

An alternative way to look at this data is to take the 32 genes with the highest rank in PGE+GMCSF/Control (from Table 3) and rank them on the basis of total intensity of PGE+GMCSF/control. This data is shown in Table 4. This removes the importance of the genes that have a high ratio increase but are not expressed to any extent in the control. This analysis highlights the importance of the chemokines as well as the calgranulins. Indeed, according to this ranking, seven of the top 13 genes are chemokines.

A further way to analyse the data is by statistical interrogation, ranking upregulated differentially expressed genes, relative to control, according to a M value which is the log of the fold increase over control. Only those genes that have a B value greater than 4 are included where the B value is the log(base 2) of odds that a gene is differentially expressed. This data is shown in Tables 5 and 6, for cells treated with HSP+GMCSF and PGE+GMCSF respectively. The data shows that although the pattern of genes stimulated by PGE+GMCSF is slightly different from those stimulated by HSP+GMCSF, there is still a predominance of chemokine stimulation, with PBP-CXCL7 being the top ranked gene in each treatment.

Figure 2:
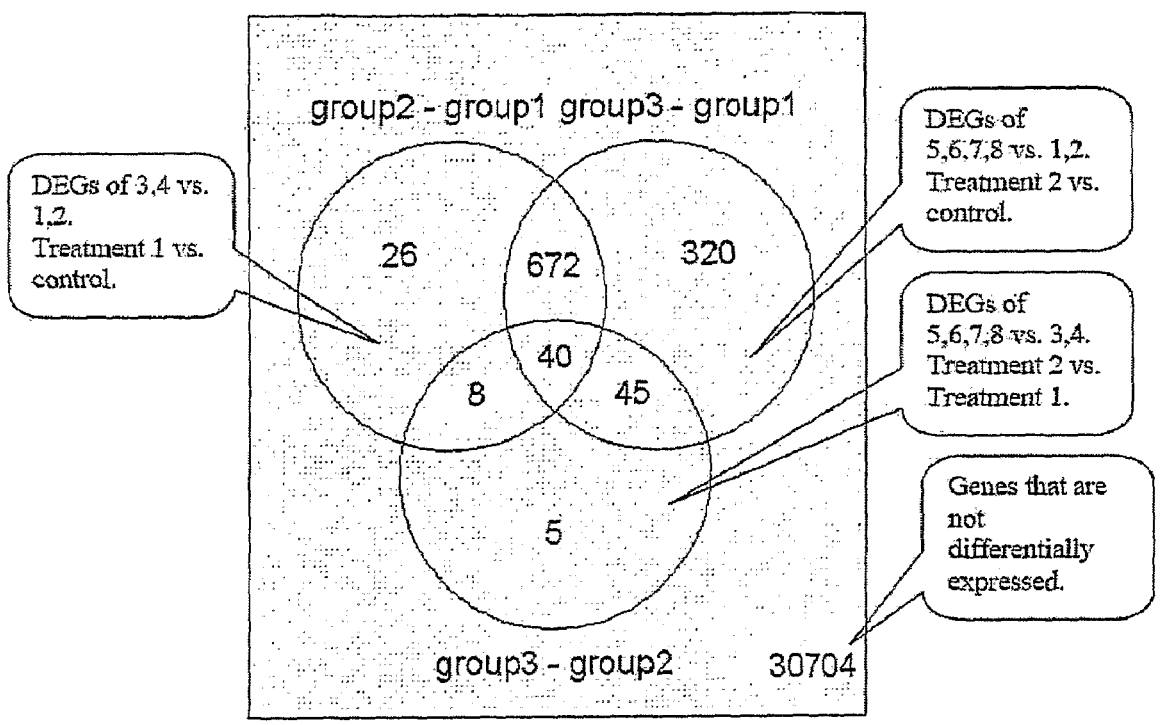

FIG. 2 is a Venn diagram showing overlap in differentially expressed genes between treatment groups GMCSF+PGE [treatment 1] and control (group 2-group 1); GMCSF+HSP [treatment 2] and control (group 3-group 1); and GMCSF+HSP [treatment 2] and GMCSF+PGE [treatment 1] (group 3-group 2). Most of the differentially expressed genes in ML1 cells treated with GMCSF+PGE relative to control (712 out of 746 genes) were also differentially expressed in ML1 cells treated with GMCSF+HSP relative to control. Indeed, there were only 98 genes that were differentially expressed between the two treatment groups GMCSF+PGE and GMCSF+HSP and, of these, 40 genes were amongst those differentially expressed relative to the control treatment. Taken together, these observations underline the high similarity of the expression profiles induced by both GMCSF+HSP and GMCSF+PGE treatments.

Table 7 lists the pathways in which the upregulated differentially expressed genes identified in Tables 5 and 6 are implicated, ranked according to significance. The table shows that for both GMCSF+HSP and GMCSF+PGE treatments, inflammation mediated by chemokine and cytokine signalling is the most significant pathway in which the differentially expressed genes have been implicated. Moreover, 12 out of the 13 pathways in which the differentially expressed genes were implicated, in cells treated with GMCSF+PGE, were also implicated for the differentially expressed genes identified in cells treated with GMCSF+HSP, again highlighting the similarity in expression profiles between the two treatments.

Figure 3:
FIG. 3 is a graph showing the synergistic action on CXCL8 (IL-8) of both PGE and human seminal plasma when combined with GMCSF. CXCL8 (CCL8) mRNA expression and CXCL8 protein release from the cells over 48 hours display this synergistic effect.

FIG. 3 is a graph showing the synergistic action on CXCL8 (CCL8, IL-8) of both PGE and human seminal plasma when combined with GMCSF on CXCL8 (CCL8, IL-8). CCL8 mRNA expression and CCL8 protein release from the cells over 48 hours display this synergistic effect.

Figure 4:
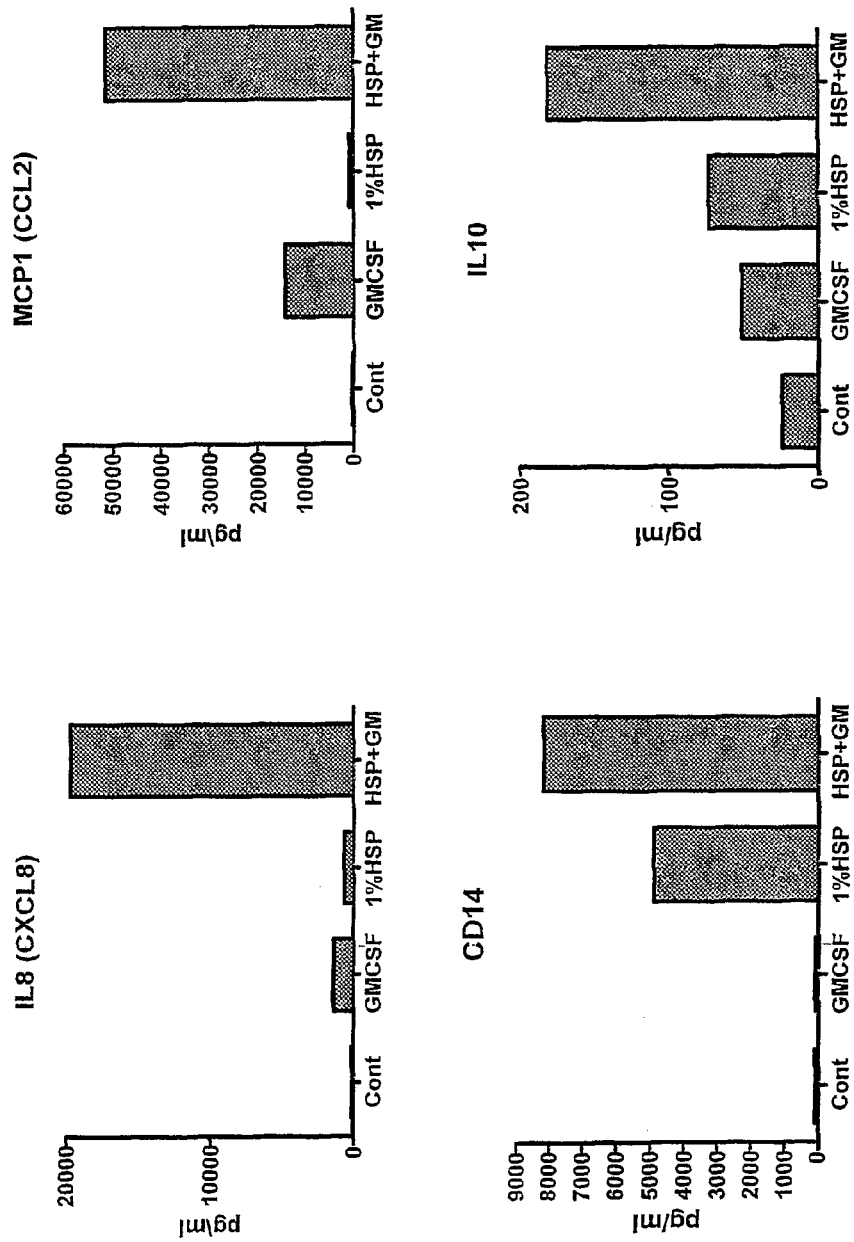
FIG. 4 is a graph showing the synergistic action of the low-molecular weight fraction of human seminal plasma (HSP) and GMCSF on chemokine/protein release from monocytic ML1 cells after 48 hours in culture.

FIG. 4 is a graph showing the synergistic action of the low-molecular weight fraction of human seminal plasma (HSP) and GMCSF on chemokine release from monocytic ML1 cells after 48 hours in culture. The low-molecular weight fraction of human seminal plasma is depleted of proteins, but contains appreciable levels of soluble CD14. This explains the relatively high levels of CD14 measured after treatment with the HSP fraction alone.

FIG. 5 is a graph showing the synergistic action of PGE and GMCSF on chemokine release from monocytic U937 cells after 48 hours in culture. The release of chemokines CXCL8 and CCL2 in response to GMCSF and PGE demonstrates that the synergistic effect of GMCSF with human seminal plasma is reproduced by PGE. GMCSF and PGE also have a synergistic effect on the release of soluble CD14 and IL-10. The relevance of IL-10 (also known as cytokine synthesis inhibitory protein) is that it is an 'inhibitory' cytokine and is likely to stop unwanted excitatory agents such as histamine being released from mast cells. CD 14 is a marker of the macrophage lineage.

FIG. 6 is a graph showing the effect of pretreatment with PGE and GMCSF on IL-8 and COX-2 expression in ML1 cells. Cells were incubated for 48 hours either with no additions or with PGE together with GMCSF. The pre-treatments were removed and the cells were washed and then three further treatments were added: control, PGE and GMCSF, and Phorbol myristoyl acetate (PMA, which is a well established differentiation agent for monocytes). Incubation was continued for a further 48 hours. The effect of the PGE and GMCSF pretreatment is preserved at the end of the 4 day period after exposure to PMA. The relevance of COX-2 expression is that this will produce further PGE which prolong the exposure to the relatively unstable PGE.

FIG. 7 is a graph showing the synergistic action of PGE and GMCSF on the expression of the pro-PBP gene from monocytic ML1 cells after 48 hours in culture. (In FIG. 6, pro-PBP is referred to as CXCL7, one of its gene products). The expression of pro-PBP in response to GMCSF and PGE demonstrates that the effect seen in the expression arrays represents true synergism. Pro-PBP expression in response to GMCSF and PGE was increased 3725 times over the control. GMCSF and PGE were also shown to have a synergistic effect on the expression of IL-10, but to a lesser extent than for pro-PBP.

Discussion

In order to identify which genes have expression levels that change in response to PGE and GMCSF the inventor conducted array experiments which presented several unexpected findings. The inventor studied the effects of a combination of human seminal plasma (HSP) and GMCSF in a monocyte cell model (ML1 cells) and examined the genes that are maximally expressed (Table 2). Table 2 shows the 32 out of 32,800 genes that have the greatest increase in expression after treatment with HSP and GMCSF.

The inventor found that:

HSP and GMCSF induce huge increases in mRNA levels of several chemokines.

The effects of HSP and forskolin differ when both are separately combined with GMCSF, showing that the increases in expression are not necessarily dependent on cAMP levels.

PGE and GMCSF induce huge increases in mRNA levels of several chemokines in a similar fashion to HSP and GMCSF.

Follow-up studies show that the induction of chemokine mRNA and protein release is a true synergistic action of E series prostaglandin and GMCSF.

Surprisingly, the top three increases in gene expression in response to HSP and GMCSF were CXCL8/IL-8 (1549 times increased), CCL2/MCP-1 (1071 times increased) and PBP CXCL7/NAP-2 (918 times increased). These findings were reproduced in subsequent quantitative PCR and protein release studies when PGE and GMCSF are used together, but not separately, indicating a true synergism. The increases in mRNA are mirrored in the increases in protein released. These increases in chemokine expression accompany those seen for the pro-tolerant cytokine IL-10.

The array studies show that the total response to PGE is not exclusively mediated by elevated intracellular cAMP levels, thus indicating the importance of PGE itself, or agonists of it such as 16,16-dimethyl PGE. Raising cAMP levels is an important part of the action of PGE and GMCSF since it appears to be the main pathway in stimulating IL-10. cAMP levels may play some part in the release of chemokines from the monocyte, since rolipram, the type IV phosphodiesterase inhibitor, has been shown to enhance IL-8 release induced by PGE and GMCSF.

The pattern of chemokine induction by PGE and GM-CSF resembles the end of the first phase of wound repair and thus such a combination may be used to accelerate wound repair.

For example, slow healing wounds, such as those in areas of the skin that are poorly vascularised, or in the elderly, could be accelerated or promoted by the local administration of a PGE or agonist thereof and GMCSF or a derivative thereof. Indeed, this combination may be therapeutically useful for accelerating or promoting wound healing in a wider range of applications including skin wounds and surgical operation wounds in the otherwise healthy patient. This combination may also be useful in wound repair in the case of gastrointestinal damage such as that associated with Crohn's disease.

The expression of the pro-platelet basic protein (pro-PBP) gene showed the third highest increase in response to HSP+ GMCSF (Table 2) and the highest increase in response to PGE+GMCSF (Table 3), and this was confirmed by the RT-PCR data shown in FIG. 7. The pro-PBP gene encodes platelet basic protein (PBP) which is a precursor of several polypeptides including CXCL7 (NAP-2), connective tissue activating peptide III (CTAPIII) and beta-thromboglobulin. Proudfoot et al (1997) states that both CXCL7 and CTAPIII are involved in the early stages of wound healing, and BTG is highly chemotactic for fibroblasts, again important in wound healing (Senior et al, 1983). This accentuates that the response to PGE and GMCSF is a pro-wound healing response. An increase in the level of the chemokine CXCL7 would be highly significant for promoting wound healing. Nevertheless, without wishing to be bound by theory, the inventor considers that it highly probable that the levels of each of CXCL7, CTAPIII and BTG are increased in response to PGE and GMCSF.

CCL2 (MCP-1) and CXCL8 (IL-8) are both known to be relevant to wound healing. FIG. 8 shows the arrival of both neutrophils and monocytes into tissue that is healing. This accords with the production of IL-8 (which attracts neutrophils) and MCP-1 (which attracts monocytes) being important in wound healing. There is also an element of angiogenesis in wound healing and the role of IL-8 and MCP-1 in this process is well described in the literature. IL-8 papers: (Koch et al 1992; Sunderkotter et al 1994; Arenberg et al. 1996) and MCP-1 papers: (Goede et al 1999; Kim et al 2005).

GMCSF has several actions, the most important and well defined is the ability to promote haematopoiesis, the expansion of leukocytes. This occurs largely in the bone marrow. The other actions include differentiation of leukocytes and a poorly-defined chemotactic action. GMCSF has been implicated in improved wound healing, particularly for ulcers (Siddiqui et al, 2000). This effect appears to involve induction of neutrophils and monocytes into the tissue but appears to be independent of the circulating levels of leukocytes (Jyung et al, 1994). There are occasional references to PGE and wound repair although they are not as consistent as those for GMCSF. Milio et al (2005) shows that $PGE_1$ improves the healing of ulcers, but this effect is thought to be due to the vasoactive and VEGF generating properties of PGE.

By contrast, the inventor considers that GMCSF is indirectly chemotactic by virtue of the stimulation of chemotactic cytokines such as CXCL8 and CCL2. In that case, the synergism between PGE and GMCSF would be very important since exploiting the synergism by adding a topical preparation of theses two agents would increase the speed and efficacy of the attraction of leukocytes and hence accelerate wound healing in a dependable manner.

Monocytic cells enter tissue relatively poorly differentiated. The cytokine milieu within the tissue plays a major part in differentiating the monocytes. The inventor considers that establishing a reservoir of PGE or an agonist thereof and GMCSF or a derivative thereof at the wound site after treatment would be particularly useful, allowing cells that are induced to migrate into the wound to be modulated by the PGE and GMCSF. One PGE agonist which might be particularly effective is 16,16-dimethyl PGE, which is resistant to the main catabolic enzyme 15-hydroxy prostaglandin dehydrogenase (Ohno et al, 1978). This compound is reported to activate all known PGE receptors.

In addition, the chemotactic cytokines produced by monocytic cells in response to this synergistic mix of PGE or an agonist thereof and GMCSF or a derivative thereof will themselves act synergistically with the PGE, thus enhancing the ingress of leukocytes (Foster et al, 1989; Colditz, 1990). Furthermore, the leukocytes that enter the tissue in response to the chemotactic signals will be relatively poorly differentiated and will mature under the influence of PGE, which will reduce the release of free-radicals by neutrophils, thus contributing to a pro-wound healing environment.

In addition to chemokine signalling, the pathway analysis in Table 7 identified angiogenesis and the Notch pathway as active components of the differential gene expression pattern in response to GMCSF and PGE. Both of these are also relevant to wound healing. Angiogenesis is critical to wound repair, facilitating the infiltration of inflammatory cells and cytokines to the site of injury, and Notch signalling has also recently been implicated in wound healing, being involved in epidermal cell differentiation (Thelu et al, 2002).

In addition, the genes with 7th and 9th highest level of increase of gene expression in Table 2 are both calgranulins. These are very relevant to wound healing as they are natural antimicrobial agents. A natural antimicrobial activity would greatly assist wound healing.

EXAMPLE 2

The Effect of PGE and GMCSF on a Rat Model of Wound Healing

Summary

Results from experiments conducted in a rat model of wound healing demonstrated a synergy between a PGE analog and GMCSF in the acceleration of wound healing. Both wound area and wound colour were monitored to assess wound healing. Administering a combination of a PGE analog and GMCSF significantly reduced the wound area by day 3 post surgery, with no significant difference observed when either treatment was administered alone. Furthermore, wound colour observations indicated a synergy between the PGE analog and GMCSF at day 10. These results confirm that locally applied PGE and GMCSF is useful in accelerating wound healing in rats.

Experimental Details

Animals Used

Male Sprague Dawley rats weighing between 250-300 grams were used as a wound healing model to assess the effects of PGE and GMCSF. 6 rats per treatment group were analysed to provide adequate data for statistical comparisons between control and treated groups. A total of 24 animals were used (4 groups of 6 rats). The four groups were control, 16,16-dimethyl PGE, GMCSF, and 16,16-dimethyl PGE+ GMCSF groups. Animals were group housed until treatment, then singly housed (so animals did not lick or chew on each other's wounds) in microisolator polycarbonate show box cages with elevated steel floors (to prevent bedding and faeces from entering the open wound sites). Two wounds were created on each animal, resulting in an "n" of 12 wounds per group.

Protocol

Following acclimatisation (5-6 days), the rats were given a subcutaneous injection of Glycopyrolate (0.01 mg/kg at 0.02 mg/mL), dose volume 0.5 mL/kg, and anesthetised with an intraperitoneal injection of a Ketamine (40 mg/kg)/Xylazine (5 mg/kg) cocktail at 45 mg/mL (ket) and 5 mg/mL (xy), dose volume 0.88 mL/kg. Adequate depth of anesthesia was assessed by a toe pinch prior to beginning surgery, such that if any movement was noted, the animals were given more anaesthesia. Surgery did not commence until the animal was adequately anesthetised. Once anesthesia was accomplished, a 6×8 cm area was shaved in the dorsal area. Following shaving, a depilatory agent (Nair) was applied to the shaved area, and allowed to remain on the skin for approximately 5 minutes. After this time, the Nair was gently scraped from the skin with a blunt spatula and any residue was removed by rinsing the skin with deionised, distilled water and wiping with gauze sponges. The shaved area was then surgically prepared with chlorhexidine and alcohol scrub.

The rat was then placed on its abdomen and positioned in such a way that the limbs were relaxed and the spine was straight. A T-shaped template was arranged on the dorsum with the stem of the T centered on the spine and the crosspiece of the T adjacent to the inferior angle of the scapulae. The inside margins of the T were traced with a Sharpie pen, such that as upside-down "L" appeared on the right side of the rat and an upside-down and backward "L" appeared on the left side of the animal. These designated the cranial border of each wound, approximately 3 cm caudal to the scapular angles, and the medial border of each wound, approximately 0.25 cm from the midline.

To make the wound template, the rim of a cap from a Corning 15 ml conical tube was placed on the area and traced using a sterile surgical marker creating a 2 cm circle within one of the upside-down L's described above. An initial incision was made with a #10 scalpel blade at the medial edge of each circle. The incision was made through the panniculus carnosus into the areolar layer of the subcutaneous loose connective tissue. The excision was continued around the entire perimeter of the circle using forceps and Metzenbaum curved scissors while taking care to avoid damaging the deep fescial layers. The skin was removed to leave a circular wound. Where necessary, hemostasis was achieved by even compression with a sterile gauze pad.

The test agent or vehicle control, was administered at three different sites under the wound bed. Group assignments and dose levels for each treatment were as detailed in Table 8. Dose levels were based on body weight.

TABLE 8

| Group No. | Number of Males | Treatment per site | Dose volume (mL/kg) | Dose solution concentration (mg/mL) |
|---|---|---|---|---|
| 1 | 6 | Control (buffered 0.9% saline) | 1.07 | N/A |
| 2 | 6 | PGE analog (400 µg/kg) | 1.06 | 0.38 mg/mL |
| 3 | 6 | GMCSF (25 µg/kg) | 1.09 | 0.023 mg/mL |
| 4 | 6 | PGE analog + GMCSF (400 µg/kg + 25 µg/kg) | 0.525 + 0.514 | 0.778 mg/mL + 0.048 mg/mL |

The wounds were not covered with any type of dressing. Approximately 30 minutes after recovery (determined by sternal recumbency and normal movement) the animals were given a subcutaneous injection of Buprenorphine (0.1 mg/kg) and transferred to individual cages with elevated stainless steel floors. Additional Buprenorphine was given every 6-8 hours as needed, then for the following 72 hours, 0.05 mg/kg was administered every 6-12 hours as needed.

The animals were monitored for any signs of pain and/or distress such as decreased appetite, decreased activity, scruffy appearance, and inability or reluctance to maintain normal hydration, in addition to monitoring the animals daily for wound infection and signs of stress. Food and water were provided ad libitum.

Animals were anesthetised with isoflurane on days 3, 7, and 10 following surgery and the wounds were measured by caliper for width and length. The width and length measurements were then multiplied to calculate wound area and the mean wound area and standard error of the mean for each treatment determined. To test for any significant difference in wound healing relative to control treatment, a two-way analysis of variance (ANOVA) test was performed on the mean wound areas. In addition to wound area, wound healing was evaluated daily by observing wound colour. Wounds were scored as being either red or brown or in two instances black or in two instances scab yellow, whereby red indicates a less healed wound than brown.

After wound evaluation on day 10, animals were sacrificed by an intercardiac injection of Beuthanasia solution (150 mg/kg) while under inhaled isoflurane. Wound sites were collected and stored in 10% neutral buffered formalin for 24 hours, before being transferred to 80% ethanol.

Results

Table 9 shows the mean wound area for each treatment group on days 3, 7 and 10, following surgery. The same data is represented in graphical format in FIG. 8. Analysis of the data using a two-way ANOVA test revealed the synergistic action of a PGE analog and GMCSF on wound healing (Table 10). Following treatment with a combination of a PGE analog (16,16-dimethyl PGE) and GMCSF, wound area was significantly reduced relative to control on day 3 post surgery. No significant difference in wound area was observed when the wound was treated with the PGE analog or GMCSF alone.

FIG. 9 illustrates the differences in wound area on day 3 post surgery, for each of the four treatments. As determined by the two-way ANOVA analysis, only a combination of the PGE analog and GMCSF resulted in a significant reduction in wound area.

FIG. 10 illustrates the daily wound colour observations for rats administered with each of the four treatments. Administering the PGE analog, GMCSF or a combination of the analog and GMCSF to the wound, all accelerated wound healing, having more consistent brown scores relative to the control treatment on days 3-5. Furthermore a synergistic action between the PGE analog and GMCSF was revealed at days 9 and 10. There were more consistent brown scores on days 9 and 10 in treatment group 4 (=9), compared to group 3 (=3) and groups 1 and 2 (=2).

TABLE 9

Comparison of treatments in the progression of wound healing. Mean wound area and standard (St.) error, as measured on days 3, 7 and 10, are listed for each treatment. The PGE analog used was 16,16-dimethyl PGE.

| Treatment | Day 3 | | Day 7 | | Day 10 | |
|---|---|---|---|---|---|---|
| | Mean wound area ($mm^2$) | St. Error | Mean wound area ($mm^2$) | St. Error | Mean wound area ($mm^2$) | St. Error |
| Control | 439.7 | 26.1 | 266.6 | 46.1 | 144.2 | 32.5 |
| PGE analog | 387.5 | 49.8 | 255.4 | 39.3 | 135.1 | 12.5 |
| GMCSF | 424.2 | 44.8 | 248.0 | 50.7 | 153.0 | 41.5 |
| PGE analog + GMCSF | 375.4 | 29.7 | 242.2 | 48.4 | 150.3 | 36.5 |

TABLE 10

Two-way analysis of variance (ANOVA) analysis of mean wound areas in table 9, testing whether there is any significant difference in wound healing progression relative to control, when each of a PGE analog, GMCSF or a combination of a PGE analog and GMCSF, are administered to the wound. The difference in wound area relative to control, the t value from the ANOVA analysis and the corresponding significance of the result, as on days 3, 7 and 10, are listed for each of the treatments.

| | Day | PGE analog | GMCSF | PGE analog + GMCSF |
|---|---|---|---|---|
| Difference in wound area relative to control | 3 | −52.21 | −15.50 | −64.27 |
| | 7 | −11.29 | −18.63 | −24.43 |
| | 10 | −9.185 | 8.761 | 6.104 |
| t value | 3 | 2.166 | 0.6744 | 2.797 |
| | 7 | 0.4685 | 0.8107 | 1.063 |
| | 10 | 0.3811 | 0.3813 | 0.2656 |
| p value | 3 | $p > 0.05$ | $p > 0.05$ | $p < 0.05$ |
| | 7 | $p > 0.05$ | $p > 0.05$ | $p > 0.05$ |
| | 10 | $p > 0.05$ | $p > 0.05$ | $p > 0.05$ |

Discussion

To determine the impact that PGE and GMCSF has on wound healing in vivo, the inventor conducted experiments on a rat model of wound healing. The inventor studied the effects of administering different treatment regimes, namely a PGE analog (16,16-dimethyl PGE), GMCSF and a combination of the PGE analog and GMCSF to a wound, and examined wound area, relative to control, on days 3, 7 and 10 post surgery. Wound colour was also scored as being red or brown on a daily basis, red wounds being less healed than brown wounds.

The inventor found that on day 3 there was a marked synergy between a PGE analog and GMCSF, resulting in a significant reduction in wound area compared to control. No significant difference in wound area was apparent when using either the PGE analog or GMCSF alone. No significant difference in wound area relative to control was observed on either of days 7 or 10, post surgery. Since the model used was one of wound healing in a normal healthy rat, the inventor considers that it is probable that on days 7 and 10, wound healing in an untreated rat had sufficiently progressed to mask any difference. In contrast, on day 3, during the first stage of wound healing, the healing process of wounds treated with PGE and GMCSF would be much more advanced relative to that in normal rats, resulting in a significant difference in wound area.

Similarly, a synergy between a PGE analog and GMCSF in accelerating wound healing was also demonstrated when the inventor assessed wound healing by colour observations. Specifically, on days 9 and 10 post surgery, wounds administered with a combination of a PGE analog and GMCSF, had more consistent brown scores, and therefore were more healed than wounds treated with either of the treatments alone.

Taken together, these results confirm that administering a combination of PGE and GMCSF to a wound accelerates the healing process. The inventor believe that administration of PGE and GMCSF accelerated wound healing by the creation of a pro wound healing environment, established by the induction of chemokines resembling the first phase of wound repair, as demonstrated in Example 1.

REFERENCES

Albala (2003) "Fibrin sealants in clinical practice". *Cardiovasc Surg.* 11 (Suppl 1): 5-11.
Arenberg, et al (1996). "Inhibition of interleukin-8 reduces tumorigenesis of human non-small cell lung cancer in SCID mice." *J Clin Invest* 97(12): 2792-802.
Brzozowski, et al (2005) "Agonist of peroxisome proliferators-activated receptor gamma (PPAR-gamma): a new compound with potent gastroprotective and ulcer healing properties". Inflammopharmacology. 13: 317-30.
Buchsel et al (2002) *Clin. J. Oncol. Nurs.* 6(4): 198-205.
Cantrell et al (1985) "Cloning, sequence, and expression of a human granulocyte/macrophage colony-stimulating factor", *Proc. Natl. Acad. Sci. U.S.A.* 82(18): 6250-6254.
Cho and Tai (2002) "Thiazolidinediones as a novel class of NAD(+)-dependent 15 hydroxyprostaglandin dehydrogenas inhibitors" Arch Biochem Biophys, 405: 247.
Clark (2003) "Fibrin glue for wound repair: facts and fancy". *Thromb Haemost.* 90(6): 1003-6.
Colditz (1990). "Effect of exogenous prostaglandin E2 and actinomycin D on plasma leakage induced by neutrophil activating peptide-1/interleukin-8." *Immunology and Cell Biology* 68: 397-403.

DiPietro et al (1998) MIP-1alpha as a critical macrophage chemoattractant in murine wound repair. *J Clin Invest* 101: 1693-1698

Engelhardt et al (1998) Chemokines IL-8, GROalpha, MCP-1, IP-10, and Mig are sequentially and differentially expressed during phase-specific infiltration of leukocyte subsets in human wound healing. *Am J Pathol* 153: 1849-1860

Foster, et al (1989). "Acute inflammatory effects of a monocyte-derived neutrophil-activating peptide in rabbit skin." *Immunology* 67(2): 181-183.

Gargett et al (2001) Focal vascular endothelial growth factor correlates with angiogenesis in human endometrium. Role of intravascular neutrophils. *Hum Reprod* 16: 1065-1075

Goede, et al (1999). "Induction of inflammatory angiogenesis by monocyte chemoattractant protein-1." *Int J Cancer* 82(5): 765-70.

Grant et al (2005) PGE/cAMP and GMCSF synergise to induce a pro-tolerance cytoidne profile in monocytic cell lines. *Biochem Biophys Res Commun* 331: 187-193

Hamilton (2002) *Trends Immunol* 23(8): 403-8.

Harvey (2005) "Wound Healing" *Orthopaedic Nursing* 24(2): 143-157.

Hong, J. P., H. D. Jung, et al. (2006). "Recombinant human epidermal growth factor (EGF) to enhance healing for diabetic foot ulcers." *Ann Plast Surg* 56(4): 394-8; discussion 399-400.

Jing et al (2004) A novel signaling pathway mediates the inhibition of CCL3/4 expression by prostaglandin E2. *J Biol Chem* 279: 55176-55186

Jyang et al (1994) "Granulocyte-macrophage colony-stimulating factor and granulocyte colony-stimulating factor: differential action on incisional wound healing". *Surgery* 115: 325-334.

Kim, et al (2005). "Inhibition of the angiogenesis by the MCP-1 (monocyte chemoattractant protein-1) binding peptide." *FEBS Lett* 579(7): 1597-601.

Koch, et al (1992). "Interleukin-8 as a macrophage-derived mediator of angiogenesis." *Science* 258(5089): 1798-801.

Lee et al (1985) "Isolation of cDNA for a human granulocyte-macrophage colony-stimulating factor by functional expression in mammalian cells" *Proc. Natl. Acad. Sci. U.S.A.* 82(13): 4360-4364.

Lionelli & Lawrence (2003) "Wound dressings". *Surg Clin North Am.* 83(3): 617-38.

Low et al (2001) "Wound healing in MIP-1alpha(−/−) and MCP-1 (−/−) mice". *Am J Pathol* 159: 457-463.

MacGillivray (2003) "Fibrin sealants and glues." *J Card Surg.* 18(6): 480-5.

Mann et al (2006) "Repression of prostaglandin dehydrogenase by epidermal growth factor and snail increases prostaglandin E2 and promotes cancer progression" *Cancer Res.* 66: 6649-59.

Menaker (2004) "Wound dressings for office-based surgery." *Facial Plast Surg.* 20(1): 91-105.

Milio et al (2005) "Efficacy of the treatment with prostaglandin E-1 in venous ulcers of the lower limbs". *J Vasc Surg* 42: 304-308.

Miyatake et al. (1985) "Structure of the chromosomal gene for granulocyte-macrophage colony stimulating factor: comparison of the mouse and human genes". *EMBO J.* 4(10): 2561-2568.

Mueller et al (2000) Neutrophils infiltrating the endometrium express vascular endothelial growth factor: potential role in endometrial angiogenesis. *Fertil Steril* 74: 107-112

Ohno H, Morikawa Y, Hirata F 1978 Studies on 15-hydroxyprostaglandin dehydrogenase with various prostaglandin analogues. *J Biochem (Tokyo)* 84: 1485-1494.

Proudfoot et al (1997) "Structure and Bioactivity of Recombinanat Human CTAP-III and NAP-2" *J Prot Chem* 16(1): 37-49.

Ritz et al (2002) *Trends Immunol* 23(8): 396-402.

Robertson & Seamark (1990) Granulocyte macrophage colony stimulating factor (GMCSF) in the uterine reproductive tract. *Reprod Fertil Develop* 2: 359-368.

Robillard et al (1994) Association of pregnancy induced hypertension with duration of sexual cohabitation before conception. *The Lancet* 344: 973-975.

Senior et al (1983) "Chemotactic activity of platelet alpha granule proteins for fibroblasts." *J Cell Biol* 96(2): 382-5.

Sheibanie et al (2004) Prostaglandin E2 induces IL-23 production in bone marrow-derived dendritic cells. *Faseb J* 18: 1318-1320

Siddiqui et al (2000) "Recombinant granulocyte macrophage colony stimulating factor (rhu-GMCSF) in the treatment of extensive leg ulcers: a case report" *Surgery* 127: 589-592.

Spotnitz & Prabhu (2005). "Fibrin sealant tissue adhesive—review and update." *J Long Term Eff Med. Implants.* 15(3): 245-70.

Strieter et al (1992) Interleukin-8—a corneal factor that induces neovascularization. *American Journal Of Pathology* 141: 1279-1284

Strieter et al (1995) The role of cxc chemokines as regulators of angiogenesis. *Shock* 4: 155-160

Sunderkotter, et al (1994). "Macrophages and angiogenesis." *J Leukoc Biol* 55(3): 410-22.

Tanaka, A., T. Nagate, et al. (2005). "Acceleration of wound healing by gelatin film dressings with epidermal growth factor." *J Vet Med Sci* 67(9): 909-13.

Thelu et al (2002). "Notch signalling is linked to epidermal cell differentiation level in basal cell carcinoma, psoriasis and wound healing." BMC Dermatol 2:7

Vermeulen et al (2005) "Systematic review of dressings and topical agents for surgical wounds healing by secondary intention." *Br J. Surg.* 92(6): 665-72.

Wong et al (1985), "Human GMCSF: molecular cloning of the complementary DNA and purification of the natural and recombinant proteins" *Science* 228 (4701): 810-815.

TABLE 2

Ranked expression of mRNA from ML1 cells treated with 1% human seminal plasma (HSP) + GMCSF divided by the control mRNA with no treatment. First 32 genes out of 32,800 ranked accordingly are shown. Chemokines are indicated in bold type.

| Rank | Gene Code | Expression ("F") | Expression (Control) | Expression (Treatment) | Treatment/Control | Gene | Type | α-Type |
|---|---|---|---|---|---|---|---|---|
| 1 | hCG16372.3 | 12,287.45 | 194.67 | 301,606.70 | 1549.32 | CXCL-8 (IL8) | ELR+ | Alpha |
| 2 | hCG29298.3 | 56,365.03 | 431.14 | 462,123.87 | 1071.86 | CCL2 (MCP1) | | Beta |
| 3 | hCG16365.2 | 33,130.82 | 316.82 | 290,913.62 | 918.23 | Pro-PBP (CXCL7; NAP-2) | ELR+ | Alpha |
| 4 | hCG2039461 | 38,284.21 | 115.19 | 40,955.91 | 355.55 | Immunoglobulin-like receptor | | |
| 5 | hCG40366.2 | 24,259.02 | 433.77 | 137,422.27 | 316.81 | OAS1 | | |
| 6 | hCG45292.2 | 5,757.07 | 318.35 | 89,565.76 | 281.34 | CD14 | | |

TABLE 2-continued

Ranked expression of mRNA from ML1 cells treated with 1% human seminal plasma (HSP) + GMCSF divided by the control mRNA with no treatment. First 32 genes out of 32,800 ranked accordingly are shown. Chemokines are indicated in bold type.

| Rank | Gene Code | Expression ("F") | Expression (Control) | Expression (Treatment) | Treatment/Control | Gene | Type | α-Type |
|---|---|---|---|---|---|---|---|---|
| 7 | hCG15465.3 | 346,898.74 | 1,242.30 | 339,984.34 | 273.67 | Calgranulin B | | |
| 8 | hCG24570.3 | 12,702.03 | 298.72 | 80,052.05 | 267.99 | IFIT4 | | |
| 9 | hCG1743776.3 | 109,591.47 | 346.56 | 91,561.37 | 264.20 | Calgranulin A (S100A8) | | |
| 10 | hCG1640186.3 | 48,569.83 | 291.21 | 73,656.88 | 252.93 | Pleckstrin homology sec 7 | | |
| 11 | hCG40366.2 | 27,489.00 | 612.14 | 151,389.24 | 247.31 | OAS1 | | |
| 12 | hCG1771418.1 | 52,554.69 | 1,911.97 | 454,626.68 | 237.78 | GIP2 (interferon-induced protein) | | |
| 13 | hCG1748235.2 | 543.71 | 186.05 | 43,799.11 | 235.42 | CCL4 (MIP1beta) | | beta |
| 14 | hCG27362.3 | 19,554.53 | 405.46 | 85,775.33 | 211.55 | OASL | | |
| 15 | hCG1789754.2 | 28,802.91 | 187.55 | 38,983.96 | 207.86 | Integrin alpha X (NM_005101) | | |
| 16 | hCG16361.2 | 3,949.28 | 264.91 | 54,768.38 | 206.74 | CXCL2 | ELR+ | alpha |
| 17 | hCG1749202.1 | 520.09 | 176.94 | 36,191.69 | 204.54 | CCL3 (MIP1alpha) | | beta |
| 18 | hCG2012695 | 31,069.68 | 189.95 | 34,326.83 | 180.72 | TRPM8 (transient cation channel) | | |
| 19 | hCG1816984.1 | 92,324.57 | 2,721.57 | 463,563.59 | 170.33 | Ferritin | | |
| 20 | hCG41471.2 | 5,449.12 | 279.9 | 41,429.94 | 148.02 | MMP1 | | |
| 21 | hCG1749202.1 | 1,118.16 | 291.21 | 39,309.80 | 134.99 | CCL3 | | |
| 22 | hCG1727099.1 | 13,176.95 | 1,755.36 | 227,611.17 | 129.67 | GIP3 | | |
| 23 | hCG1643352.3 | 13,509.43 | 373.97 | 47,886.39 | 128.05 | Ribonucleoprotein | | |
| 24 | hCG40171.2 | 27,221.55 | 491.68 | 62,896.17 | 127.92 | IRF ISGF3 gamma sub-unit | | |
| 25 | hCG24571.3 | 47,333.38 | 1,770.34 | 220,965.77 | 124.82 | IFIT 1 (interferon induced protein) | | |
| 26 | hCG23571.3 | 25,438.51 | 307.36 | 37,210.44 | 121.06 | TYROBP (protein Y kinase binding protein) | | |
| 27 | hCG26002.2 | 8,981.58 | 342.77 | 41,243.12 | 120.32 | IER 3 (immediate early response) | | |
| 28 | hCG33721.2 | 250,337.23 | 3,795.09 | 427,922.50 | 112.76 | Serpin B2 | | |
| 29 | hCG28054.3 | 185.17 | 604.86 | 67,458.16 | 111.53 | Cathepsin O (NM_001334) | | |
| 30 | hCG1807133.1 | 4,811.64 | 469.35 | 51,378.72 | 109.47 | CXCL7-like | | |
| 31 | hCG1788111.2 | 3,472.06 | 236.37 | 24,968.92 | 105.63 | TRIM 22 (tripartite motif containing) | | |
| 32 | hCG2010232.2 | 59,530.86 | 931.36 | 97,204.08 | 104.37 | T cell receptor gamma chain | | |

In column 3, Expression "F" is expression in the presence of forskolin + GMCSF. In column 4, the "Control" is expression in the absence of treatment. In column 5, the "Treatment" is HSP + GMCSF. In column 8, "Type" is the chemokine type. In column 9, "α-Type" is the type of α chemokine.

TABLE 3

Ranked expression of mRNA from ML1 cells treated with PGE + GMCSF and 1% HSP + GMCSF divided by the control (mRNA expression with no treatment). The top 32 genes out of 32,800 ranked according to the ratio of PGE + GMCSF/control are shown. Chemokines are indicated in bold type.

| Rank | Gene code | Control | Treatment "P" | Treatment "H" | Ratio "P" | Ratio "H" | Gene | Type | α-Type |
|---|---|---|---|---|---|---|---|---|---|
| 1 | hCG16365.2 | 1535 | 1074816 | 841633 | 700.4 | 548.4 | Pro-PBP (CXCL7; NAP-2) | alpha | ELR+ |
| 2 | hCG41471.2 | 1686 | 750104 | 710894 | 445.0 | 421.7 | MMP1 | | |
| 3 | hCG2039077 | 336 | 140580 | 73517 | 418.8 | 219.0 | AF086204-1 - unassigned | | |
| 4 | hCG26571.3 | 176 | 42252 | 32861 | 240.5 | 187.0 | EPM-protein 1 | | |
| 5 | hCG29298.3 | 6847 | 1063685 | 1350173 | 155.4 | 197.2 | CCL2 (MCP-1) | beta | |
| 6 | hCG2039724.1 | 668 | 97343 | 46261 | 145.8 | 69.3 | MHC-1 | | |
| 7 | hCG16366.3 | 244 | 33072 | 57966 | 135.5 | 237.5 | CXCL3 | alpha | ELR+ |
| 8 | hCG16372.3 | 1687 | 221659 | 509116 | 131.4 | 301.8 | CXCL8 | alpha | ELR+ |
| 9 | hCG16263.2 | 3317 | 404895 | 688215 | 122.1 | 207.5 | IL-1Beta | | |
| 10 | hCG39885.3 | 681 | 81732 | 117266 | 120.1 | 172.3 | COX-2 | | |
| 11 | hCG1743776.3 | 6885 | 794219 | 697255 | 115.4 | 101.3 | Calgranulin A (S100A8) | | |
| 12 | hCG29304.2 | 586 | 66039 | 43517 | 112.6 | 74.2 | CCL7 | beta | |
| 13 | hCG14693.4 | 521 | 57424 | 49126 | 110.2 | 94.2 | IgGFcRec | | |
| 14 | hCG1748235.2 | 1722 | 178566 | 166816 | 103.7 | 96.9 | CCL4 MIP 1bta | beta | |
| 15 | hCG1805714.2 | 139 | 13598 | 13632 | 98.1 | 98.4 | IFIT | | |
| 16 | hCG15468.3 | 465 | 44929 | 18742 | 96.6 | 40.3 | Calgranulin C | | |
| 17 | hCG38806.4 | 419 | 36100 | 29363 | 86.2 | 70.1 | ATP6VOD2 | | |
| 18 | hCG41965.2 | 293 | 24310 | 74172 | 82.9 | 252.9 | TNFAIP6 | | |
| 19 | hCG1749202.1 | 1595 | 128682 | 168075 | 80.7 | 105.4 | CCL3 | beta | |
| 20 | hCG91957.2 | 214 | 16722 | 20206 | 78.2 | 94.5 | FPR1 | | |
| 21 | hCG1653946.3 | 1445 | 111172 | 53305 | 76.9 | 36.9 | KIR3DL2 | | |
| 22 | hCG29301.2 | 481 | 36861 | 51160 | 76.7 | 106.4 | CCL8 | beta | |
| 23 | hCG45292.2 | 1566 | 114615 | 420325 | 73.2 | 268.4 | CD14 | | |
| 24 | hCG20766.3 | 282 | 20445 | 15154 | 72.5 | 53.8 | ZPF36L1 | | |
| 25 | hCG1775764.2 | 1012 | 72187 | 65044 | 71.4 | 64.3 | C5R1 | | |
| 26 | hCG1685968.2 | 457 | 32015 | 36514 | 70.1 | 79.9 | FAP | | |
| 27 | hCG1749202.1 | 1873 | 114829 | 144856 | 61.3 | 77.3 | CCL3 | beta | |
| 28 | hCG1773845.2 | 444 | 26799 | 31618 | 60.3 | 71.2 | CLECSF12 | | |
| 29 | hCG16361.2 | 1929 | 111484 | 139955 | 57.8 | 72.6 | CXCL2 | alpha | ELR+ |
| 30 | hCG15465.3 | 30966 | 1741317 | 1486169 | 56.2 | 48.0 | Calgranulin B | | |
| 31 | hCG27362.3 | 1948 | 108526 | 100746 | 55.7 | 51.7 | OASL | | |
| 32 | hCG26002.2 | 1605 | 86823 | 291778 | 54.1 | 181.8 | IER3 (immediate early response) | | |

In column 3, the "Control" is expression in the absence of treatment. In column 4, Treatment "P" is the mean expression with the treatment PGE + GMCSF. In column 5, Treatment "H" is the mean expression with the treatment HSP + GMCSF. In column 6, the ratio "P" is Treatment P/control. In column 7, the ratio "H" is Treatment H/control. In column 9, "Type" is the chemokine type. In column 10, "α-Type" is the type of α chemokine.

TABLE 4

Same data as shown in Table 3 but ranked according to the expression levels after treatment with PGE + GMCSF.

| Rank | Gene code | Control | Treatment "P" | Treatment "H" | Ratio "P" | Ratio "H" | Gene | Type | α-Type |
|---|---|---|---|---|---|---|---|---|---|
| 1 | hCG15465.3 | 30966 | 1741317 | 1486169 | 56.2 | 48.0 | Calgranulin B | | |
| 2 | hCG16365.2 | 1535 | 1074816 | 841633 | 700.4 | 548.4 | Pro-PBP (CXCL7; NAP-2) | alpha | ELR+ |
| 3 | hCG29298.3 | 6847 | 1063685 | 1350173 | 155.4 | 197.2 | CCL2 (MCP-1) | beta | |
| 4 | hCG1743776.3 | 6885 | 794219 | 697255 | 115.4 | 101.3 | Calgranulin A (S100A8) | | |
| 5 | hCG41471.2 | 1686 | 750104 | 710894 | 445.0 | 421.7 | MMP1 | | |
| 6 | hCG16263.2 | 3317 | 404895 | 688215 | 122.1 | 207.5 | IL-1Beta | | |
| 7 | hCG16372.3 | 1687 | 221659 | 509116 | 131.4 | 301.8 | CXCL8 | alpha | ELR+ |
| 8 | hCG1748235.2 | 1722 | 178566 | 166816 | 103.7 | 96.9 | CCL4 MIP 1bta | beta | |
| 9 | hCG2039077 | 336 | 140580 | 73517 | 418.3 | 219.0 | AF086204-1 - unassigned | | |
| 10 | hCG1749202.1 | 1595 | 128682 | 168075 | 80.7 | 105.4 | CCL3 | beta | |
| 11 | hCG1749202.1 | 1873 | 114829 | 144856 | 61.3 | 77.3 | CCL3 | beta | |
| 12 | hCG45292.2 | 1566 | 114615 | 420325 | 73.2 | 268.4 | CD14 | | |
| 13 | hCG16361.2 | 1929 | 111484 | 139955 | 57.8 | 72.6 | CXCL2 | alpha | ELR+ |
| 14 | hCG1653946.3 | 1445 | 111172 | 53305 | 76.9 | 36.9 | KIR3DL2 | | |
| 15 | hCG27362.3 | 1948 | 108526 | 100746 | 55.7 | 51.7 | OASL | | |
| 16 | hCG2039724.1 | 668 | 97343 | 46261 | 145.8 | 69.3 | MHC-1 | | |
| 17 | hCG26002.2 | 1605 | 86823 | 291778 | 54.1 | 181.8 | IER3 (immediate early response) | | |
| 18 | hCG39885.3 | 681 | 81732 | 117266 | 120.1 | 172.3 | COX-2 | | |
| 19 | hCG1775764.2 | 1012 | 72187 | 65044 | 71.4 | 64.3 | C5R1 | | |
| 20 | hCG29304.2 | 586 | 66039 | 43517 | 112.6 | 74.2 | CCL7 | beta | |
| 21 | hCG14693.4 | 521 | 57424 | 49126 | 110.2 | 94.2 | IgGFcRec | | |
| 22 | hCG15468.3 | 465 | 44929 | 18742 | 96.6 | 40.3 | Calgranulin C | | |
| 23 | hCG26571.3 | 176 | 42252 | 32861 | 240.5 | 187.0 | EPM-protein 1 | | |
| 24 | hCG29301.2 | 481 | 36861 | 51160 | 76.7 | 106.4 | CCL8 | beta | |
| 25 | hCG38806.4 | 419 | 36100 | 29363 | 86.2 | 70.1 | ATP6VOD2 | | |
| 26 | hCG16366.3 | 244 | 33072 | 57966 | 135.5 | 237.5 | CXCL3 | alpha | ELR+ |
| 27 | hCG1685968.2 | 457 | 32015 | 36514 | 70.1 | 79.9 | FAP | | |
| 28 | hCG1773845.2 | 444 | 26799 | 31618 | 60.3 | 71.2 | CLECSF12 | | |
| 29 | hCG41965.2 | 293 | 24310 | 74172 | 82.9 | 252.9 | TNFAIP6 | | |
| 30 | hCG20766.3 | 282 | 20445 | 15154 | 72.5 | 53.8 | ZPF36L1 | | |
| 31 | hCG91957.2 | 214 | 16722 | 20206 | 78.2 | 94.5 | FPR1 | | |
| 32 | hCG1805714.2 | 139 | 13598 | 13632 | 98.1 | 98.4 | IFIT | | |

TABLE 5

Upregulated differentially expressed genes in ML1 cells treated with human seminal plasma and GMCSF. All genes listed have a B value (log of odds that gene is differentially expressed) between 16 and 4. Genes are ranked by log (base 2) fold increase over control (=M). Chemokines are in bold.

| Rank | Gene code | M value | Gene_Symbol | Gene_name |
|---|---|---|---|---|
| 1 | hCG16365.2 | 8.93385091 | PPBP | pro-platelet basic protein (chemokine (C—X—C motif) ligand 7) |
| 2 | hCG41471.2 | 8.604634256 | MMP1 | matrix metalloproteinase 1 (interstitial collagenase) |
| 3 | hCG28054.3 | 7.963598618 | TDO2 | tryptophan 2,3-dioxygenase |
| 4 | hCG16372.3 | 7.944683552 | IL8 | interleukin 8 |
| 5 | hCG45292.2 | 7.937987537 | CD14 | CD14 antigen |
| 6 | hCG29298.3 | 7.815216428 | CCL2 | chemokine (C-C motif) ligand 2 |
| 7 | hCG16263.2 | 7.701122934 | IL1B | interleukin 1, beta |
| 8 | hCG26002.2 | 7.18274869 | IER3 | immediate early response 3 |
| 9 | hCG41965.2 | 6.770179641 | TNFAIP6 | tumor necrosis factor, alpha-induced protein 6 |
| 10 | hCG1743776.3 | 6.751260279 | S100A8 | S100 calcium binding protein A8 (calgranulin A) |
| 11 | hCG1749202.1 | 6.493376565 | MGC12815; CCL3L1; CCL3 | chemokine (C-C motif) ligand 3-like, centromeric; chemokine (C-C motif) |
| 12 | hCG1748235.2 | 6.487151346 | CCL4L; CCL4L1; CCL4 | chemokine (C-C motif) ligand 4-like; chemokine (C-C motif) ligand 4-like 1, |
| 13 | hCG16366.3 | 6.439762592 | CXCL3 | chemokine (C—X—C motif) ligand 3 |
| 14 | hCG1749202.1 | 6.133980403 | MGC12815; CCL3L1; CCL3 | chemokine (C-C motif) ligand 3-like, centromeric; chemokine (C-C motif) ligand 3-like 1 |
| 15 | hCG16361.2 | 6.054330528 | CXCL2 | chemokine (C—X—C motif) ligand 2 |
| 16 | hCG15465.3 | 5.832844199 | S100A9 | S100 calcium binding protein A9 (calgranulin B) |
| 17 | hCG29301.2 | 5.829427864 | CCL8 | chemokine (C-C motif) ligand 8 |
| 18 | hCG38536.2 | 5.764711686 | OAS2 | 2'-5'-oligoadenylate synthetase 2, 69/71 kDa |
| 19 | hCG1775764.2 | 5.690958588 | C5R1 | complement component 5 receptor 1 (C5a ligand) |
| 20 | hCG24571.4 | 5.689657206 | IFIT1 | interferon-induced protein with tetratricopeptide repeats 1 |
| 21 | hCG26571.3 | 5.65314799 | EMP1 | epithelial membrane protein 1 |
| 22 | hCG27362.3 | 5.597280752 | OASL | 2'-5'-oligoadenylate synthetase-like |
| 23 | hCG37146.3 | 5.549826612 | MAFB | v-maf musculoaponeurotic fibrosarcoma oncogene homolog B (avian) |
| 24 | hCG2039724.1 | 5.547287913 | KIR2DL4 | killer cell immunoglobulin-like receptor, two domains, long cytoplasmic tail, 4 |
| 25 | hCG29304.2 | 5.540329937 | CCL7 | chemokine (C-C motif) ligand 7 |
| 26 | hCG1685968.2 | 5.486323192 | FAP | fibroblast activation protein, alpha |

TABLE 5-continued

Upregulated differentially expressed genes in ML1 cells treated with human seminal plasma and GMCSF. All genes listed have a B value (log of odds that gene is differentially expressed) between 16 and 4. Genes are ranked by log (base 2) fold increase over control (=M). Chemokines are in bold.

| Rank | Gene code | M value | Gene_Symbol | Gene_name |
|---|---|---|---|---|
| 27 | hCG1811532.1 | 5.476198695 | CYBB | cytochrome b-245, beta polypeptide (chronic granulomatous disease) |
| 28 | NM_000265.1 | 5.419070991 | NCF1 | neutrophil cytosolic factor 1 (47 kDa, chronic granulomatous disease, autosomal 1) |
| 29 | hCG40406.4 | 5.301003464 | MS4A4A | membrane-spanning 4-domains, subfamily A, member 4 |
| 30 | hCG1773845.2 | 5.258973039 | CLECSF12 | C-type (calcium dependent, carbohydrate-recognition domain) lectin, superfamily member 12 |
| 31 | hCG38806.4 | 5.249174911 | ATP6V0D2 | ATPase, H+ transporting, lysosomal 38 kDa, V0 subunit d isoform 2 |
| 32 | hCG401128.3 | 5.231473543 | SAMSN1 | SAM domain, SH3 domain and nuclear localisation signals, 1 |
| 33 | hCG40366.2 | 5.201651243 | OAS1 | 2',5'-oligoadenylate synthetase 1, 40/46 kDa |
| 34 | hCG40366.2 | 5.188249726 | OAS1 | 2',5'-oligoadenylate synthetase 1, 40/46 kDa |
| 35 | hCG1771418.1 | 5.157927748 | G1P2 | interferon, alpha-inducible protein (clone IFI-15K) |
| 36 | hCG32604.3 | 5.08977752 | CCL15; CCL14 | chemokine (C-C motif) ligand 15; chemokine (C-C motif) ligand 14 |
| 37 | hCG32869.2 | 5.079225507 | TREM1 | triggering receptor expressed on myeloid cells 1 |
| 38 | hCG91957.2 | 5.043339643 | FPR1 | formyl peptide receptor 1 |
| 39 | hCG1653946.3 | 5.036744379 | KIR3DL2 | killer cell immunoglobulin-like receptor, three domains, long cytoplasmic tail, 2 |
| 40 | hCG17305.3 | 5.01312062 | ANXA1 | annexin A1 |
| 41 | hCG1643352.4 | 4.957035039 | IFIT2 | interferon-induced protein with tetratricopeptide repeats 2 |
| 42 | hCG23054.3 | 4.936901531 | C3 | complement component 3 |
| 43 | hCG21858.3 | 4.711525699 | EMR1 | egf-like module containing, mucin-like, hormone receptor-like 1 |
| 44 | hCG24570.3 | 4.709879318 | IFIT4 | interferon-induced protein with tetratricopeptide repeats 4 |
| 45 | hCG28814.2 | 4.703448877 | AGRP | agouti related protein homolog (mouse) |
| 46 | hCG17885.3 | 4.683694276 | SAT | spermidine/spermine N1-acetyltransferase |

TABLE 6

Upregulated differentially expressed genes in ML1 cells treated with PGE and GMCSF. All genes listed have a B value (log of odds that gene is differentially expressed) between 16 and 4. Genes are ranked by log (base 2) fold increase over control (=M). Chemokines are in bold.

| Rank | Gene ID | M | Gene_Symbol | Gene_name |
|---|---|---|---|---|
| 1 | hCG16365.2 | 9.116667998 | PPBP | pro-platelet basic protein (chemokine (C—X—C motif) ligand 7) |
| 2 | hCG41471.2 | 8.498953633 | MMP1 | matrix metalloproteinase 1 (interstitial collagenase) |
| 3 | hCG29298.3 | 7.277272275 | CCL2 | chemokine (C-C motif) ligand 2 |
| 4 | hCG1743776.3 | 6.839847289 | S100A8 | S100 calcium binding protein A8 (calgranulin A) |
| 5 | hCG16263.2 | 6.818705295 | IL1B | interleukin 1, beta |
| 6 | hCG2039724.1 | 6.440423681 | KIR2DL4 | killer cell immunoglobulin-like receptor, two domains, long cytoplasmic tail, 4 |
| 7 | hCG1748235.2 | 6.40982755 | CCL4L; CCL4L1; CCL4 | chemokine (C-C motif) ligand 4-like, chemokine (C-C motif) ligand 4 |
| 8 | hCG1749202.1 | 6.015476593 | MGC12815; CCL3L1; CCL3 | chemokine (C-C motif) ligand 3-like, centromeric; chemokine (C-C motif) ligand 3 |
| 9 | hCG29304.2 | 5.967129184 | CCL7 | chemokine (C-C motif) ligand 7 |
| 10 | hCG1653946.3 | 5.921964763 | KIR3DL2 | killer cell immunoglobulin-like receptor, three domains, long cytoplasmic tail, 2 |
| 11 | hCG45292.2 | 5.90135795 | CD14 | CD14 antigen |
| 12 | hCG15465.3 | 5.884393418 | S100A9 | S100 calcium binding protein A9 (calgranulin B) |
| 13 | hCG1749202.1 | 5.678203475 | MGC12815; CCL3L1; CCL3 | chemokine (C-C motif) ligand 3-like, centromeric; chemokine (C-C motif) ligand 3 |
| 14 | hCG1775764.2 | 5.64642221 | C5R1 | complement component 5 receptor 1 (C5a ligand) |
| 15 | hCG15468.3 | 5.603871529 | S100A12 | S100 calcium binding protein A12 (calgranulin C) |
| 16 | hCG16361.2 | 5.599895712 | CXCL2 | chemokine (C—X—C motif) ligand 2 |
| 17 | hCG27362.3 | 5.557018766 | OASL | 2'-5'-oligoadenylate synthetase-like |
| 18 | hCG16366.3 | 5.519024088 | CXCL3 | chemokine (C—X—C motif) ligand 3 |
| 19 | hCG24571.4 | 5.408109813 | IFIT1 | interferon-induced protein with tetratricopeptide repeats 1 |
| 20 | hCG37146.3 | 5.372415096 | MAFB | v-maf musculoaponeurotic fibrosarcoma oncogene homolog B (avian) |
| 21 | hCG38806.4 | 5.348661832 | ATP6V0D2 | ATPase, H+ transporting, lysosomal 38 kDa, V0 subunit d isoform 2 |
| 22 | hCG29301.2 | 5.296640273 | CCL8 | chemokine (C-C motif) ligand 8 |
| 23 | hCG38536.2 | 5.196696132 | OAS2 | 2'-5'-oligoadenylate synthetase 2, 69/71 kDa |
| 24 | hCG401128.3 | 5.187529179 | SAMSN1 | SAM domain, SH3 domain and nuclear localisation signals, 1 |
| 25 | hCG1685968.2 | 5.112451655 | FAP | fibroblast activation protein, alpha |
| 26 | hCG32604.3 | 4.993856247 | CCL15; CCL14 | chemokine (C-C motif) ligand 15; chemokine (C-C motif) ligand 14 |
| 27 | hCG41965.2 | 4.982568671 | TNFAIP6 | tumor necrosis factor, alpha-induced protein 6 |
| 28 | hCG40366.2 | 4.930633164 | OAS1 | 2',5'-oligoadenylate synthetase 1, 40/46 kDa |
| 29 | NM_000265.1 | 4.91148143 | NCF1 | neutrophil cytosolic factor 1 (47 kDa, chronic granulomatous disease, autosomal 1) |
| 30 | hCG1773845.2 | 4.886076247 | CLECSF12 | C-type (calcium dependent, carbohydrate-recognition domain) lectin, superfamily member 12 |

TABLE 6-continued

Upregulated differentially expressed genes in ML1 cells treated with PGE and GMCSF. All genes listed have a B value (log of odds that gene is differentially expressed) between 16 and 4. Genes are ranked by log (base 2) fold increase over control (=M). Chemokines are in bold.

| Rank | Gene ID | M | Gene_Symbol | Gene_name |
|---|---|---|---|---|
| 31 | hCG40366.2 | 4.870129729 | OAS1 | 2',5'-oligoadenylate synthetase 1, 40/46 kDa |
| 32 | hCG20766.3 | 4.785519943 | ZFP36L1 | zinc finger protein 36, C3H type-like 1 |
| 33 | hCG1643352.4 | 4.774203837 | IFIT2 | interferon-induced protein with tetratricopeptide repeats 2 |
| 34 | hCG21858.3 | 4.749666067 | EMR1 | egf-like module containing, mucin-like, hormone receptor-like 1 |
| 35 | hCG17305.3 | 4.702785336 | ANXA1 | annexin A1 |
| 36 | hCG1771418.1 | 4.690391105 | G1P2 | interferon, alpha-inducible protein (clone IFI-15K) |
| 37 | hCG91957.2 | 4.621356993 | FPR1 | formyl peptide receptor 1 |
| 38 | hCG28054.3 | 4.580307838 | TDO2 | tryptophan 2,3-dioxygenase |
| 39 | hCG23989.3 | 4.51872897 | ADM | adrenomedullin |
| 40 | hCG2039725.1 | 4.467516336 | KIR3DL1 | killer cell immunoglobulin-like receptor, three domains, long cytoplasmic tail, 1 |
| 41 | hCG22355.3 | 4.381229804 | FOS | v-fos FBJ murine osteosarcoma viral oncogene homolog |
| 42 | hCG17885.3 | 4.363580937 | SAT | spermidine/spermine N1-acetyltransferase |
| 43 | hCG1640186.3 | 4.338650651 | PSCDBP | pleckstrin homology, Sec7 and coiled-coil domains, binding protein |
| 44 | hCG40015.3 | 4.310876817 | MMP9 | matrix metalloproteinase 9 (gelatinase B, 92 kDa gelatinase, 92 kDa type IV collagenase) |
| 45 | hCG20262.3 | 4.274571734 | FCAR | Fc fragment of IgA, receptor for |
| 46 | hCG2043692 | 4.191289942 | LILRA3 | leukocyte immunoglobulin-like receptor, subfamily A (without TM domain), member 3 |
| 47 | hCG15367.4 | 4.132148241 | CDKN1A | cyclin-dependent kinase inhibitor 1A (p21, Cip1) |
| 48 | hCG1641561.3 | 4.108763818 | LOC129607 | hypothetical protein LOC129607 |
| 49 | hCG1811781.1 | 4.091544629 | DDX58 | DEAD (Asp-Glu-Ala-Asp) box polypeptide 58 |
| 50 | hCG1818087.1 | 4.083365328 | GPR34 | G protein-coupled receptor 34 |
| 51 | hCG1812154.1 | 4.078776584 | SLC7A7 | solute carrier family 7 (cationic amino acid transporter, y+ system), member 7 |
| 52 | hCG2039461 | 4.061719891 | PILRA | paired immunoglobin-like type 2 receptor alpha |
| 53 | hCG16367.1 | 4.025258186 | PF4 | platelet factor 4 (chemokine (C—X—C motif) ligand 4) |

TABLE 7

Pathways in which upregulated differentially expressed genes in ML1 cells are implicated, for treatment 1 vs control, treatment 2 vs control and treatment 1 vs treatment 2.

| Pathway | DEGs upregulated in Treatment 1 vs. control, p-values |
|---|---|
| Inflammation mediated by chemokine and cytokine signaling pathway | 1.99E−14 |
| Alzheimer disease-presenilin pathway | 1.61E−06 |
| Integrin signalling pathway | 2.68E−05 |
| Plasminogen activating cascade | 1.30E−04 |
| Notch signaling pathway | 1.96E−04 |
| Angiogenesis | 2.79E−04 |
| Interleukin signaling pathway | 3.37E−04 |
| B cell activation | 3.31E−03 |
| Heterotrimeric G-protein signaling pathway-Gq alpha and Go alpha mediated pathway | 3.46E−03 |
| Axon guidance mediated by semaphorins | 3.89E−03 |
| Apoptosis signaling pathway | 4.26E−03 |
| T cell activation | 8.87E−03 |
| Interferon-gamma signaling pathway | 9.10E−03 |

| Pathway | DEGs upregulated in Treatment 2 vs. control, p-values |
|---|---|
| Inflammation mediated by chemokine and cytokine signaling pathway | 2.78E−17 |
| Alzheimer disease-presenilin pathway | 1.04E−06 |
| Angiogenesis | 4.44E−05 |
| Plasminogen activating cascade | 5.80E−05 |
| Interleukin signaling pathway | 1.17E−04 |
| Integrin signalling pathway | 1.76E−04 |
| Blood coagulation | 9.90E−04 |
| Axon guidance mediated by semaphorins | 1.10E−03 |
| Notch signaling pathway | 1.25E−03 |
| Heterotrimeric G-protein signaling pathway-Gq alpha and Go alpha mediated pathway | 1.51E−03 |
| Apoptosis signaling pathway | 4.01E−03 |
| Interferon-gamma signaling pathway | 5.40E−03 |
| JAK/STAT signaling pathway | 6.07E−03 |

TABLE 7-continued

Pathways in which upregulated differentially expressed genes in ML1 cells are implicated, for treatment 1 vs control, treatment 2 vs control and treatment 1 vs treatment 2.

| | |
|---|---|
| T cell activation | 6.93E−03 |
| Heterotrimeric G-protein signaling pathway-Gi alpha and Gs alpha mediated pathway | 8.79E−03 |

| Pathway | DEGs upregulated in Treatment 2 vs. Treatment1, p-values |
|---|---|
| Inflammation mediated by chemokine and cytokine signaling pathway | 7.05E−04 |

The invention claimed is:

1. A method of promoting healing of a wound in a patient, the method comprising administering to the patient, within the first four days following wounding, (i) a prostaglandin E (PGE) or an agonist thereof and (ii) granulocyte-macrophage colony stimulating factor (GMCSF) or a derivative thereof, wherein the method does not include administering a skin stem cell to the patient and said administering is carried out by applying to the wound a wound dressing or bandage that comprises (i) and (ii).

2. A method according to claim 1 wherein the PGE or agonist thereof is any one of $PGE_1$, $PGE_2$, 19-hydroxy $PGE_1$, 19-hydroxy $PGE_2$, 16,16-dimethyl PGE, dinoprostone, misoprostol, alprostadil and limaprost.

3. A method according to claim 1 wherein the GMCSF is human GMCSF having the amino acid sequence of SEQ ID NO: 2, or a naturally occurring variant thereof.

4. A method according to claim 1 wherein the GMCSF is sargramostim or molgramostim.

5. A method according to claim 1 further comprising administering at least one antimicrobial agent to the patient.

6. A method according to claim 5 wherein the antimicrobial agent is an antibacterial agent, an antifungal agent or an antiviral agent.

7. A method according to claim 6 wherein the antibacterial agent is selected from gentamicin, ampicillin, benzypenicillin, benethamine penicillin, benzathine penicillin, phenethicillin, phenoxy-methyl penicillin, procaine penicillin, cloxacillin, flucloxacillin, methicillin sodium, amoxicillin, bacampicillin hydrochloride, ciclacillin, mezlocillin, pivampicillin, talampicillin hydrochloride, carfecillin sodium, piperacillin, ticarcillin, mecillinam, pirmecillinan, cefaclor, cefadroxil, cefotaxime, cefoxitin, cefsulodin sodium, ceftazidime, ceftizoxime, cefuroxime, cephalexin, cephalothin, cephamandole, cephazolin, cephradine, cefpirome, latamoxef disodium, aztreonam, glycylcyclines, chlortetracycline hydrochloride, clomocycline sodium, demeclocydine hydrochloride, doxycycline, lymecycline, minocycline, oxytetracycline, amikacin, framycetin sulphate, neomycin sulphate, netilmicin, tobramycin, colistin, sodium fusidate, fupirocin, polymyxin B sulphate, spectinomycin, vancomycin, teicoplanin, calcium sulphaloxate, sulphametopyrazine, sulphadiazine, sulphadimidine, sulphaguanidine, sulphaurea, capreomycin, metronidazole, tinidazole, cinoxacin, ciprofloxacin, norfloxacin, nitrofurantoin, hexamine, streptomycin, carbenicillin, colistimethate, polymyxin B, furazolidone, nalidixic acid, trimethoprim-sulphamethoxazole, clindamycin, lincomycin, cycloserine, isoniazid, ethambutol, ethionamide, pyrazinamide, meropenem and imipenem.

8. A method according to claim 6 wherein the antifungal agent is selected from miconazole, ketoconazole, itraconazole, fluconazole, amphotericin, flucytosine, griseofulvin, natamycin and nystatin.

9. A method according to claim 6 wherein the antiviral agent is selected from acyclovir, AZT, ddI, amantadine hydrochloride, inosine pranobex and vidarabine.

10. A method according to claim 5 wherein the antimicrobial agent is administered locally to the patient at the site of the wound.

11. A method according to claim 1 further comprising administering an analgesic agent or an anesthetic agent locally to the patient at the site of the wound.

12. A method according to claim 11 wherein the analgesic agent is selected from methylsalicylate, salicylic acid, dyclonine and aloe vera.

13. A method according to claim 11 wherein the anesthetic is selected from benzocaine, lidocaine, xylocalne and butamben picrate.

14. A method according to claim 1 wherein the wound is an external wound.

15. A method according to claim 1 wherein said administering further comprises administering to the patient one or more of an antimicrobial agent, analgesic agent, and anesthetic agent.

16. A method according to claim 15 wherein said administering of (i) the PGE or agonist thereof, and (ii) GMCSF or derivative thereof, is carried out simultaneously with said administering of one or more of the antimicrobial agent, analgesic agent, and anesthetic agent.

17. A method according to claim 1 wherein the wound dressing or bandage further comprises an antimicrobial agent, analgesic agent, or anesthetic agent.

* * * * *